(12) United States Patent
Oh

(10) Patent No.: US 11,576,688 B2
(45) Date of Patent: Feb. 14, 2023

(54) TIBIAL ALIGNMENT DEVICE AND UNIT THEREOF

(71) Applicant: Corentec Co., Ltd., Chungcheongnam-do (KR)

(72) Inventor: Seung Hun Oh, Seoul (KR)

(73) Assignee: Corentec Co., Ltd., Chungcheongnam-do (KR)

( * ) Notice: Subject to any disclaimer, the term of this patent is extended or adjusted under 35 U.S.C. 154(b) by 203 days.

(21) Appl. No.: 17/259,394

(22) PCT Filed: Jul. 9, 2019

(86) PCT No.: PCT/KR2019/008445
§ 371 (c)(1),
(2) Date: Jan. 11, 2021

(87) PCT Pub. No.: WO2020/013584
PCT Pub. Date: Jan. 16, 2020

(65) Prior Publication Data
US 2021/0282791 A1  Sep. 16, 2021

(30) Foreign Application Priority Data

Jul. 10, 2018 (KR) ........................ 10-2018-0080025

(51) Int. Cl.
*A61B 17/16* (2006.01)
*A61B 17/17* (2006.01)
*A61B 17/00* (2006.01)

(52) U.S. Cl.
CPC ........ *A61B 17/1675* (2013.01); *A61B 17/171* (2013.01); *A61B 17/1764* (2013.01); *A61B 2017/00407* (2013.01)

(58) Field of Classification Search
CPC combination set(s) only.
See application file for complete search history.

(56) References Cited

U.S. PATENT DOCUMENTS 8,758,354 B2 * 6/2014 Habegger ............ A61B 17/157
606/88

FOREIGN PATENT DOCUMENTS

JP  2016-049462 A  4/2016
JP  2018-507074 A  3/2018
(Continued)

OTHER PUBLICATIONS

International Search Report dated Oct. 28, 2019, issued in PCT Application No. PCT/KR2019/008445, filed Jul. 9, 2019.
(Continued)

*Primary Examiner* — Sameh R Boles
(74) *Attorney, Agent, or Firm* — Workman Nydegger

(57) ABSTRACT

A tibial alignment device includes an upper part for coupling with a tibial cutting guide and a lower part coupled to the upper part to be vertically slidable, wherein the upper part includes a cutting guide coupling part configured to mount the tibial cutting guide, and a connection part to connect the upper part and the lower part, and the lower part includes an ankle forceps part, wherein the cutting guide coupling part includes a fastening member for coupling to the tibial cutting guide, and a reception member to slidably receive the fastening member, wherein the fastening member includes a coupling part that protrudes to be coupled to the tibial cutting guide, the reception member includes a coupling part that protrudes to be coupled to the tibial cutting guide, and the coupling part of the fastening member is capable of adjusting a gap with respect to the coupling part of the reception member.

18 Claims, 16 Drawing Sheets

(56) References Cited

FOREIGN PATENT DOCUMENTS

| | | |
|---|---|---|
| JP | 2018-086200 A | 6/2018 |
| KR | 10-2005-0103776 A | 11/2005 |
| KR | 10-1422678 B1 | 7/2014 |

OTHER PUBLICATIONS

Written Opinion dated Oct. 28, 2019, issued in PCT Application No. PCT/KR2019/008445, filed Jul. 9, 2019.

* cited by examiner

TIBIAL ALIGNMENT DEVICE AND UNIT THEREOF

TECHNICAL FIELD

The present disclosure relates to a total knee arthroplasty used for a knee joint including a tibia and a femur of a subject to be treated. More particularly, the present disclosure relates to a tibial alignment device including an upper part configured to be capable of being coupled to a tibial cutting guide during a total knee arthroplasty, and a lower part coupled to the upper part to be vertically slidable, wherein the upper part includes a cutting guide coupling part configured to mount the tibial cutting guide on the upper part, and a connection part configured to connect the upper part and the lower part to each other, and the lower part includes an ankle forceps part fixed to an ankle of a subject to be treated so as to fix the tibial alignment device, wherein the cutting guide coupling part is capable of being coupled to or separated from the cutting guide at various angles, wherein the cutting guide coupling part includes a fastening member configured to be capable of being coupled to the tibial cutting guide so as to be vertically movable, and a reception member configured to slidably receive the fastening member, wherein the fastening member includes a coupling part that protrudes in an insertion direction of the cutting guide coupling part at an upper end of the fastening member to be inserted into and coupled to the tibial cutting guide, the reception member includes a coupling part that protrudes in the insertion direction of the cutting guide coupling part at an upper end of the reception member to be inserted into and coupled to the tibial cutting guide, and the coupling part of the fastening member is configured to be capable of adjusting a gap with respect to the coupling part of the reception member so as to be detached from and attached to the tibial cutting guide at various angles.

BACKGROUND ART

A knee joint is a joint formed by a femur, a tibia, and a patella, which are the three bones surrounding the knee, and corresponds to a key joint related to movements using legs, such as walking or running using joint movements and supporting the weight of a person.

An articular cartilage is present at the end of a femur, and a meniscus is present at the end of a tibia. When the cartilage is damaged due to extreme exercise, aging, or the like, bones may come into direct contact with each other, which may cause severe pain.

Total knee arthroplasty is a surgery in which a part of a femur and a tibia is incised and an artificial knee joint is inserted when a knee joint is damaged. A surgical procedure for an artificial knee joint is performed by connecting a femur joint member to the end of the femur, fixedly inserting a tibia element into the end of the tibia, and installing a bearing member thereon. In such an artificial knee replacement surgery, accurate osteotomy of a damaged knee is very important in order to prevent side effects after surgery and to extend the life of the replaced artificial knee.

Accordingly, during a total knee arthroplasty, before cutting a proximal tibia portion of a subject to be treated, a rod-shaped tibial alignment assembly, the length of which is adjustable, is fixed to an ankle of the subject to be treated at one side thereof and a tibial cutting guide is fixed to the other side of the tibial alignment assembly, and is compared with the proximal tibia of a subject to be treated so as to determine an accurate cutting surface.

The tibia alignment device needs to be configured such that the length thereof is accurately adjustable according to a subject to be treated, which is directly connected to the accuracy and effectiveness of a surgical procedure. In addition, the tibial alignment device should be configured to be easily coupled to and separated from the tibial cutting guide to ensure ease of the surgical procedure and to perform an accurate and safe surgical procedure by preventing collision between surgical instruments so as to maintain aligned positions thereof.

However, the prior art has problems in that it is difficult to assemble or disassemble the tibial alignment device to and from a cutting guide, and in that it is difficult to finely adjust an alignment length. Specifically, in the case of existing instruments, since the radius or path of assembly and disassembly between the tibial cutting guide and the tibial alignment device is limited to a straight line, it is difficult to secure ease of the surgery procedure due to the difficulty in detaching and attaching of devices during surgery. In particular, due to the narrow disassembly radius of the tibial alignment device, collisions occur between other surgical instruments during disassembly, resulting in a problem in that the positions of the surgical instruments aligned to provide information on a cutting surface are disturbed or coupling is released. As a result, surgery is inaccurately performed, the deterioration of the treatment effect and pain of the patient are caused, and in severe cases, reoperation is required, resulting in time and economic loss to a subject to be treated.

In addition, the conventional tibial alignment device uses a bolt or a rachet in a portion for adjusting the length of the alignment rod. However, due to the pitch of the screw or a unit interval of grooves in the rachet, it is difficult to accurately adjust a height, resulting in problems related to accurate procedure, ease of surgery, operation progress, and pain and financial burden of a patient in a total knee arthroplasty.

In addition, cleaning of surgical instruments is important for safety reasons such as infection, and thus the instruments should be designed to have high cleanability. However, the conventional tibia alignment device does not have a separate cleaning groove in an ankle forceps part (ankle clamp) that is directly coupled to an ankle portion of a subject to be treated, and has various components coupled to each other. Thus, cleaning is not easily performed in gaps where washing water has difficulty in reaching, and there is a risk of bacterial infection due to incomplete cleaning.

U.S. Pat. No. 8,758,354 B2 discloses a tibial alignment device illustrated in FIG. 1. Referring to FIG. 1, the tibial alignment device is a device for providing information on an accurate cutting surface during tibia proximal cutting.

However, as pointed out above, since the conventional tibial alignment device described above is assembled to or disassembled from the tibial cutting guide only in the direction of a straight line, it is difficult to detach or attach the tibial alignment device and to smoothly remove the tibial cutting guide, and the tibial alignment device collides with other instruments during the surgical procedure. In addition, since the part that adjusts the coupling length of an upper rod (proximal rod) and a lower rod (distal rod) is configured in the form of a rachet, it is difficult to accurately adjust the length. In addition, the ankle forceps part (ankle clamp) also does not have structures such as a cleaning groove that facilitates cleaning of the device before and after surgery, so it is not possible to assure a safe procedure free of infection by bacteria or the like.

Therefore, the necessity of introducing a tibial alignment device is increasing, wherein the tibial alignment device is easily assembled to and disassembled from a tibial cutting guide, enables accurate height adjustment, and facilitates cleaning of the ankle forceps part so that an accurate and safe total knee arthroplasty can be performed.

DETAILED DESCRIPTION OF THE INVENTION

Technical Problem

The present disclosure has been conceived in order to solve the problems described above.

An objective of the present disclosure is to provide a tibial alignment device including: an upper part configured to be capable of being coupled to a tibial cutting guide during a total knee arthroplasty; and a lower part coupled to the upper part to be vertically slidable, wherein the upper part includes a cutting guide coupling part configured to mount the tibial cutting guide on the upper part, and a connection part configured to connect the upper part and the lower part to each other, and the lower part includes an ankle forceps part fixed to an ankle of a subject to be treated so as to fix the tibial alignment device, whereby an operator is informed of the accurate location of the tibial cutting surface during the procedure of the total knee arthroplasty. Another objective of the present disclosure is to provide a tibial alignment device, wherein the cutting guide coupling part is capable of being coupled to or separated from the tibial cutting guide at various angles, whereby the convenience and safety of the procedure can be improved by increasing the radial range for coupling and disassembling the tibial cutting guide and tibia alignment device.

Another objective of the present disclosure is to provide a tibial alignment device, wherein the cutting guide coupling part includes a fastening member configured to be capable of being coupled to the tibial cutting guide so as to be vertically movable, and a reception member configured to slidably receive the fastening member, whereby the tibial alignment device is movably coupled with the tibial cutting guide.

Another objective of the present disclosure is to provide a tibial alignment device, wherein the fastening member includes a coupling part that protrudes in an insertion direction of the cutting guide coupling part at an upper end of the fastening member to be inserted into and coupled to the tibial cutting guide, the reception member includes a coupling part that protrudes in the insertion direction of the cutting guide coupling part at an upper end of the reception member to be inserted into and coupled to the tibial cutting guide, and the coupling part of the fastening member is configured to be capable of adjusting a gap with respect to the coupling part of the reception member so that the tibial alignment device can be detachably coupled to the tibial cutting guide at various angles.

Another objective of the present disclosure is to provide a tibial alignment device, wherein the gap between the coupling part of the fastening member and the coupling part of the reception member is widened, and thus the coupling parts are placed in a locked state in which the coupling parts are firmly coupled with the tibial cutting guide, and the gap between the coupling part of the fastening member and the coupling part of the reception member is narrowed, and thus the coupling parts are placed in an unlocked state in which the coupling parts are loosely coupled to the tibia cutting guide, whereby the tibial alignment device improves the convenience of the surgery procedure by enabling an operator to easily insert and fix the coupling part through the manipulation of the locked state and the unlocked state.

Another objective of the present disclosure is to provide a tibial alignment device, wherein the cutting guide coupling part includes a lever member configured to adjust the gap between the coupling part of the fastening member and the coupling part of the reception member, whereby even with a small force, the coupling part of the fastening member is pushed up and fixed, which enables the operator to easily check the locked state and the unlocked state and to switch between the locked state and the unlocked state.

Another objective of the present disclosure is to provide a tibial alignment device including a rotating body that allows the lever member to be fixed and rotated with respect to the reception member, thereby enabling switching between the states.

Another object of the present disclosure is to provide a tibial alignment device including a leaf spring part configured to press the fastening member upward in the locked state, whereby it is possible to prevent damage to the lever member and to fix the fastening member during the rotation of the lever member by increasing the gap between the fastening member and the reception member.

Another object of the present disclosure is to provide a tibial alignment device including a handle part, which enables the operator to easily switch between the locked and unlocked states.

Another object of the present disclosure is to provide a tibial alignment device including a rotation prevention step configured to prevent the rotation of the lever member in the locked state and to maintain the locked state after coupling, whereby it is possible to prevent separation of the cutting guide coupling part during the surgery procedure, and thus to secure a safe surgery procedure.

Another object of the present disclosure is to provide a tibial alignment device including a groove so as to provide a space that allows the leaf spring part to move downward so that the lever member can rotate.

Another objective of the present disclosure is to provide a tibial alignment device, wherein the cutting guide coupling part includes close contact means configured to tighten the gap between the coupling part of the fastening member and the coupling part of the reception member in the unlocked state, whereby in the unlocked state, the separation between the fastening member and the reception member is prevented, thereby enabling an easy surgery procedure.

Another objective of the present disclosure is to provide a tibial alignment device, wherein the coupling part of the fastening member has a coupling surface including a protruding surface one end of which protrudes upward, whereby separation of the fastening member coupling portion is prevented after the coupling of the cutting guide coupling part.

Another objective of the present disclosure is to provide a tibial alignment device, wherein the coupling surface includes a concave surface formed in a curved surface and recessed to an inside of the coupling part, and a convex surface extending from the concave surface and protruding to an outside of the coupling part, the convex surface constituting the protruding surface, whereby in the locked state, the convex surface improves the fixing force of the coupling part, and enables the insertion and removal of the coupling part to be smoothly performed in the unlocked state.

Another objective of the present disclosure is to provide a tibial alignment device, wherein the fastening member includes a stopper configured to limit an insertion depth of the coupling part, thereby enabling an operator to easily perform a surgery procedure.

Another objective of the present disclosure is to provide a tibial alignment device, wherein the upper part includes a fine adjustment part configured to be capable of finely adjusting a coupling height of the cutting guide, thereby enabling accurate setting of a cutting surface so as to improve the accuracy of a surgery procedure.

Another objective of the present disclosure is to provide a tibial alignment device, wherein the lower part includes a height adjustment part so that the coupling length between the upper and lower parts can be adjusted.

Another objective of the present disclosure is to provide a tibial alignment device, wherein the height adjustment part includes a first member so as to enable the connection part of the upper part and the connection part of the lower part to be connected and fixed to each other.

Another objective of the present disclosure is to provide a tibial alignment device, wherein the height adjustment part includes a second member so that the vertical movement of the connection part of the upper part can be adjusted.

Another objective of the present disclosure is to provide a tibial alignment device, wherein the height adjustment part includes an elastic member so that a height adjusted by an operator can be maintained by the second member.

Another objective of the present disclosure is to provide a tibial alignment device, wherein when the connection part is in contact with the second member, the second member is placed in the locked state in which the lower rod is fixed, and when the connection part of the upper part and the second member forms a gap therebetween, the second member is placed in the unlocked state in which the connection part of the upper part is vertically slidable, whereby a surgery procedure is facilitated through mutual switching between the unlocked state and the unlocked state.

Another objective of the present disclosure is to provide a tibial alignment device, wherein the second member includes a contact part so as to provide a frictional force through contact with the connection part of the upper part so that the connection part of the upper part can be fixed.

Another objective of the present disclosure is to provide a tibial alignment device, wherein the second member includes a rotation coupling part so as to fix the second member to the first member and to rotate the second member so that the connection part of the upper part and the second member can be brought into contact with each other.

Another objective of the present disclosure is to provide a tibial alignment device, wherein the second member includes a handle part, which is capable of facilitating adjustment of the locked state and the unlocked state of the second member.

Another objective of the present disclosure is to provide a tibial alignment device, wherein the contact portion includes a reception hole through which the connection part of the upper part passes, and the reception hole is formed to allow the connection part of the upper part and the second member to come into contact when the second member is in the locked state, whereby the fixing force in the locked state is improved by increasing the contact area with the connection part of the upper part.

Another objective of the present disclosure is to provide a tibial alignment device, wherein the ankle forceps part includes an ankle forceps to be firmly fixed to an ankle of a subject to be treated.

Another objective of the present disclosure is to provide a tibial alignment device, wherein the ankle forceps part includes an ankle forceps connection part configured to connect the ankle forceps and the connection part of the lower part, and a sliding adjustment part configured to slide the ankle forceps connection part in an anterior or posterior direction of the subject to be treated, so that the angle formed by the tibial alignment device and the tibia of the subject to be treated can be adjusted.

Another objective of the present disclosure is to provide a tibial alignment device, wherein the ankle forceps part includes a rachet button so as to fix the position of the ankle forceps connection part.

Another objective of the present disclosure is to provide a tibial alignment device, wherein the ankle forceps part includes a connection bolt so as to prevent separation of the rachet button.

Another objective of the present disclosure is to provide a tibial alignment device, wherein the ankle forceps part includes a cleaning groove so as to improve cleaning efficiency by allowing smooth inflow of washing water.

Technical Solution

In order to achieve the objects of the present disclosure, the present disclosure is implemented by embodiments having features as follows.

According to an embodiment of the present disclosure, a tibial alignment device includes an upper part configured to be capable of being coupled to a tibial cutting guide during a total knee arthroplasty, and a lower part coupled to the upper part to be vertically slidable, wherein the upper part includes a cutting guide coupling part configured to mount the tibial cutting guide on the upper part, and a connection part configured to connect the upper part and the lower part to each other.

According to another embodiment of the present disclosure, the cutting guide coupling part is capable of being coupled to or separated from the tibial cutting guide at various angles.

According to another embodiment of the present disclosure, the cutting guide coupling part includes a fastening member configured to be capable of being coupled to the tibial cutting guide so as to be vertically movable, and a reception member configured to slidably receive the fastening member.

According to another embodiment of the present disclosure, the fastening member includes a coupling part that protrudes in an insertion direction of the cutting guide coupling part at an upper end of the fastening member to be inserted into and coupled to the tibial cutting guide, the reception member includes a coupling part that protrudes in the insertion direction of the cutting guide coupling part at an upper end of the reception member to be inserted into and coupled to the tibial cutting guide, and the coupling part of the fastening member is configured to be capable of adjusting a gap with respect to the coupling part of the reception member so that the tibial alignment device can be detached from and attached to the tibial cutting guide at various angles.

According to another embodiment of the present disclosure, the gap between the coupling part of the fastening member and the coupling part of the reception member is widened, and thus the coupling parts are placed in a locked state in which the coupling parts are firmly coupled with the tibial cutting guide, and the gap between the coupling part of the fastening member and the coupling part of the reception member is narrowed, and thus the coupling parts are placed in an unlocked state in which the coupling parts are loosely coupled to the tibia cutting guide.

According to another embodiment of the present disclosure, the cutting guide coupling part includes a lever member configured to adjust the gap between the coupling part of the fastening member and the coupling part of the reception member.

According to another embodiment of the present disclosure, the lever member includes a rotating body part configured to enable rotation of the lever member, a leaf spring part configured to press the fastening member upward in the locked state, a handle part configured to be capable of adjusting the locked state and the unlocked state of the lever member, a rotation prevention step configured to prevent rotation of the lever member in the locked state, and a groove providing a space in which the leaf spring part is movable downward to the lower side so that the lever member can rotate.

According to another embodiment of the present disclosure, the cutting guide coupling part includes close contact means configured to tighten the gap between the coupling part of the fastening member and the coupling part of the reception member in coupling parts of the fastening member and the reception member are in the locked state.

According to another embodiment of the present disclosure, the coupling part of the fastening member has a coupling surface including a protruding surface one end of which protrudes upward.

According to another embodiment of the present disclosure, the coupling surface includes a concave surface formed in a curved surface and recessed to an inside of the coupling part, and a convex surface extending from the concave surface and protruding to an outside of the coupling part, the convex surface constituting the protruding surface.

According to another embodiment of the present disclosure, the fastening member includes a stopper configured to limit an insertion depth of the coupling part.

According to another embodiment of the present disclosure, the upper part includes a fine adjustment part configured to be capable of finely adjusting a height of the cutting guide.

According to another embodiment of the present disclosure, the lower part includes a height adjustment part configured to be capable of adjusting a coupling length between the upper and lower parts, and a connection part connecting the height adjustment part and the ankle forceps part, and the height adjustment part includes a first member configured to connect the connection part of the upper part and the connection part of the lower part to each other, a second member configured to adjust a vertical movement of the connection part of the upper part, and an elastic member configured to fix a position of the second member.

According to another embodiment of the present disclosure, when the connection part of the upper part is in contact with the second member, the second member is placed in the locked state in which the lower rod is fixed, and when the connection part of the upper part and the second member forms a gap therebetween, the second member is placed in the unlocked state in which the connection part of the upper part is vertically slidable.

According to another embodiment of the present disclosure, the second member includes a contact part configured to come into contact with the connection part of the upper part, a rotation coupling part configured to rotate the second member, and a handle part configured to be capable of adjusting the locked state and the unlocked state of the second member.

According to another embodiment of the present disclosure, the contact portion includes a reception hole through which the connection part of the upper part passes, and the reception hole is formed to allow the connection part of the upper part and the second member to come into contact when the second member is in the locked state.

According to another embodiment of the present disclosure, the ankle forceps part includes a hook-shaped ankle forceps fixed to an ankle of a subject to be treated, an ankle forceps connection part configured to connect the ankle forceps and the connection part of the lower part to each other, a sliding adjustment part configured to slide the ankle forceps connection part in an anterior or posterior direction of the subject to be treated, a rachet button configured to fix a position of the ankle forceps connection part, and a connection bolt configured to prevent separation of the rachet button.

According to another embodiment of the present disclosure, the ankle forceps part has a washing groove configured to facilitate inflow of washing water so as to increase washing efficiency.

According to another embodiment of the present disclosure, the sliding adjustment part includes a cleaning groove penetrating both side surfaces thereof into which the rachet button is inserted, and the rachet button includes a cleaning groove penetrating both side surfaces of a lower end thereof into which the connection bolt is inserted.

Advantageous Effects

The present disclosure is capable of obtaining the following effects through a combination of the above-described embodiments and the configurations to be described below and a use relationship therebetween.

The present disclosure provides a tibial alignment device including: an upper part configured to be capable of being coupled to a tibial cutting guide during a total knee arthroplasty; and a lower part coupled to the upper part to be vertically slidable, wherein the upper part includes a cutting guide coupling part configured to mount the tibial cutting guide on the upper part, and a connection part configured to connect the upper part and the lower part to each other, and the lower part includes an ankle forceps part fixed to an ankle of a subject to be treated so as to fix the tibial alignment device. Therefore, an operator can be informed of the accurate location of the tibial cutting surface during the procedure of the total knee arthroplasty.

According to the present disclosure, the cutting guide coupling unit can be coupled to or separated from the tibia cutting guide at various angles so as to increase the range of the assembling and disassembling radius of the tibial cutting guide and the tibial alignment device. Therefore, the convenience and safety of a surgery procedure can be improved.

According to the present disclosure, the cutting guide coupling part includes a fastening member configured to be capable of being coupled to the tibial cutting guide so as to be vertically movable, and a reception member configured to slidably receive the fastening member. Therefore, the tibial alignment device can be movably coupled with the tibial cutting guide.

According to the present disclosure, the fastening member includes a coupling part that protrudes in an insertion direction of the cutting guide coupling part at an upper end of the fastening member to be inserted into and coupled to the tibial cutting guide, the reception member includes a coupling part that protrudes in the insertion direction of the cutting guide coupling part at an upper end of the reception member to be inserted into and coupled to the tibial cutting guide, and the coupling part of the fastening member is configured to be capable of adjusting a gap with respect to the coupling part of the reception member. Therefore, the tibial alignment device can be detachably coupled to the tibial cutting guide at various angles.

According to the present disclosure, the gap between the coupling part of the fastening member and the coupling part of the reception member is widened, and thus the coupling parts are placed in a locked state in which the coupling parts are firmly coupled with the tibial cutting guide, and the gap between the coupling part of the fastening member and the coupling part of the reception member is narrowed, and thus the coupling parts are placed in an unlocked state in which the coupling parts are loosely coupled to the tibia cutting guide. Therefore, the convenience of the surgery procedure can be improved by enabling an operator to easily insert and fix the coupling part through the manipulation of the locked state and the unlocked state.

According to the present disclosure, the cutting guide coupling part includes a lever member configured to adjust the gap between the coupling part of the fastening member and the coupling part of the reception member. Therefore, even with a small force, the coupling part of the fastening member can be pushed up and fixed, which enables the operator to easily check the locked state and the unlocked state and to switch between the locked state and the unlocked state.

According to the present disclosure, the tibial alignment device includes a rotating body part that enables rotation of the lever member. Therefore, it is possible to fix and rotate the lever member with respect to the reception member, thereby enabling switching between the states.

According to the present disclosure, a leaf spring part configured to press the fastening member upward in the locked state is included. Therefore, it is possible to prevent damage to the lever member and to fix the fastening member during the rotation of the lever member by increasing the gap between the coupling parts of the fastening member and the reception member.

According to the present disclosure, the tibial alignment device includes a handle part. Therefore, it is possible for an operator to easily switch between the locked and unlocked states.

According to the present disclosure, the tibial alignment device includes a rotation prevention step configured to prevent the rotation of the lever member in the locked state and to maintain the locked state after coupling. Therefore, it is possible to prevent separation of the cutting guide coupling part during the surgery procedure, and thus to secure a safe surgery procedure.

According to the present disclosure, the tibial alignment device includes a groove. Therefore, it is possible to provide a space that allows the leaf spring part to move downward so that the lever member can rotate.

According to the present disclosure, the cutting guide coupling part includes close contact means configured to tighten the gap between the coupling part of the fastening member and the coupling part of the reception member in the unlocked state. Therefore, in the unlocked state, it is possible to prevent the separation between the fastening member and the reception member, thereby enabling an easy surgery procedure.

According to the present disclosure, the coupling part of the fastening member has a coupling surface including a protruding surface one end of which protrudes upward. Therefore, it is possible to prevent separation of the coupling member coupling portion after the coupling of the cutting guide coupling part.

According to the present disclosure, the coupling surface includes a concave surface formed in a curved surface and recessed to an inside of the coupling part, and a convex surface extending from the concave surface and protruding to an outside of the coupling part, the convex surface constituting the protruding surface. Therefore, in the locked state, the convex surface improves the fixing force of the coupling part, and enables the insertion and removal of the coupling part to be smoothly performed in the unlocked state.

According to the present disclosure, the fastening member includes a stopper configured to limit an insertion depth of the coupling part. Therefore, it is possible for an operator to easily perform a surgery procedure.

According to the present disclosure, the upper part includes a fine adjustment part configured to be capable of finely adjusting a coupling height of the cutting guide. Therefore, it is possible to accurately set a cutting surface so as to improve the accuracy of a surgery procedure.

According to the present disclosure, the lower part includes a height adjustment part. Therefore, it is possible to adjust the coupling length between the upper and lower parts.

According to the present disclosure, the height adjustment part includes a first member. Therefore, it is possible to connect and fix the connection part of the upper part and the connection part of the lower part to each other.

According to the present disclosure, the height adjustment part includes a second member. Therefore, it is possible to adjust the vertical movement of the connection part of the upper part.

According to the present disclosure, the height adjustment part includes an elastic member. Therefore, it is possible to maintain a height adjusted by an operator by the second member.

According to the present disclosure, when the connection part is in contact with the second member, the second member is placed in the locked state in which the lower rod is fixed, and when the connection part of the upper part and the second member forms a gap therebetween, the second member is placed in the unlocked state in which the connection part of the upper part is vertically slidable. Therefore, a surgery procedure can be facilitated through mutual switching between the locked state and the unlocked state.

According to the present disclosure, the second member includes a contact part so as to provide a frictional force through contact with the connection part of the upper part. Therefore, the connection part of the upper part can be fixed.

According to the present disclosure, the second member includes a rotation coupling part so as to fix the second member to the first member and to rotate the second member. Therefore, it is possible to bring the connection part of the upper part and the second member into contact with each other.

According to the present disclosure, the second member includes a handle part. Therefore, it is possible to facilitate adjustment of the locked state and the unlocked state of the second member.

According to the present disclosure, the contact portion includes a reception hole through which the connection part of the upper part passes, and the reception hole is formed to allow the connection part of the upper part and the second member to come into contact when the second member is in the locked state. It is possible to improve the fixing force in the locked state by increasing the contact area with the connection part of the upper part.

According to the present disclosure, the ankle forceps part includes an ankle forceps. Thus, the ankle forceps part can be firmly fixed to an ankle of a subject to be treated.

According to the present disclosure, the ankle forceps part includes an ankle forceps connection part configured to connect the ankle forceps and the connection part of the lower part, and a sliding adjustment part configured to slide the ankle forceps connection part in an anterior or posterior direction of the subject to be treated. Therefore, it is possible to adjust the angle formed by the tibial alignment device and the tibia of the subject to be treated.

According to the present disclosure, the ankle forceps part includes a rachet button. Therefore, it is possible to fix the position of the ankle forceps connection part.

According to the present disclosure, the ankle forceps part includes a connection bolt. Therefore, it is possible to prevent separation of the rachet button.

According to the present disclosure, the ankle forceps part includes a cleaning groove. Thus, it is possible to improve cleaning efficiency by allowing smooth inflow of washing water.

MODE FOR CARRYING OUT THE INVENTION

Figure 1:
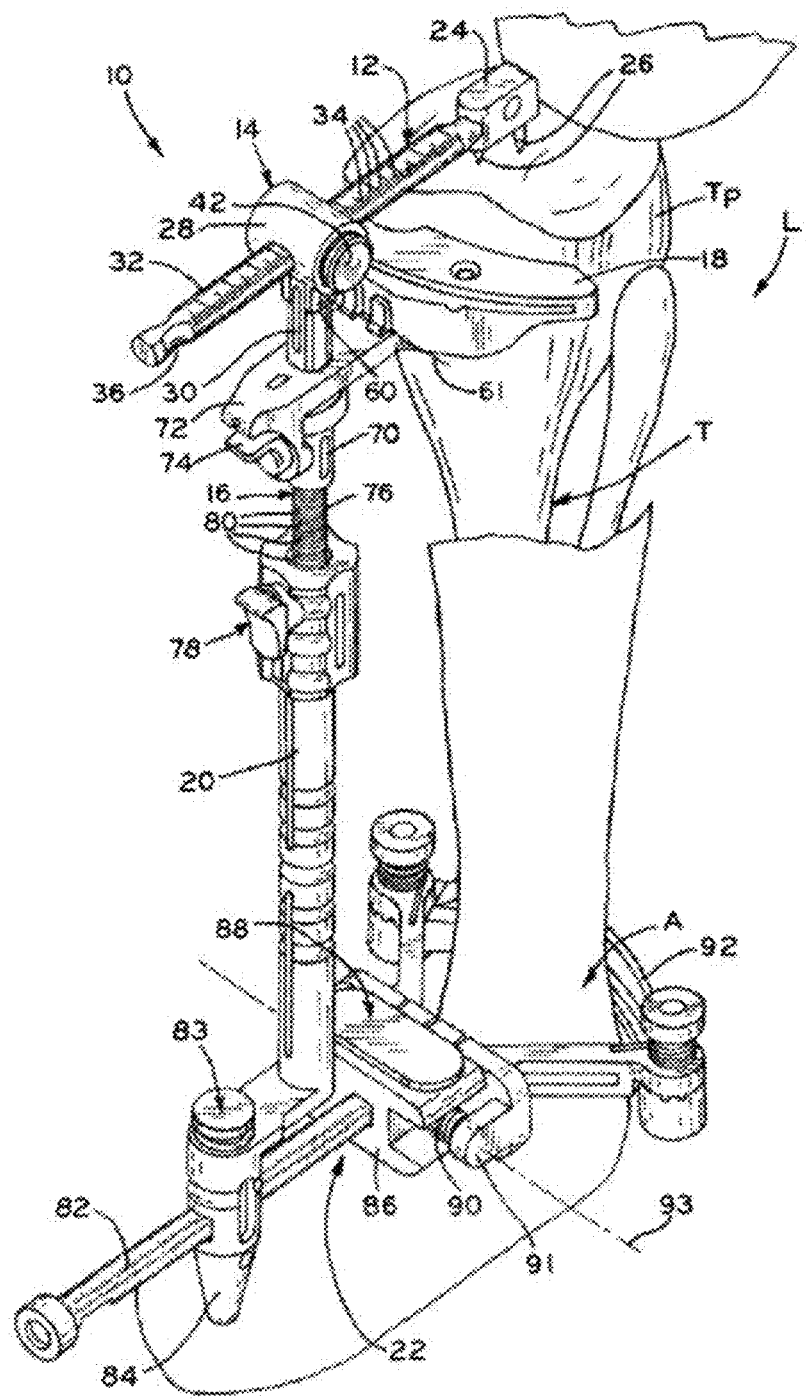
FIG. 1 is a view illustrating an embodiment of a conventional tibial alignment device.

Hereinafter, a tibial alignment device of the present disclosure will be described in detail with reference to the accompanying drawings. It shall be noted that the same elements in the drawings are denoted by the same reference numerals if possible. In the following description, a detailed description of a well-known function or construction will be omitted when it may make the subject matter of the present disclosure unnecessarily unclear. Unless defined otherwise, all terms used herein have the same meaning as the general meaning of the terms understood by a person ordinarily skilled in the art to which this disclosure belongs and, when the general meaning is in conflict with the meaning of the terms used herein, the meaning of the terms follows the definition used in the specification.

Figure 2:
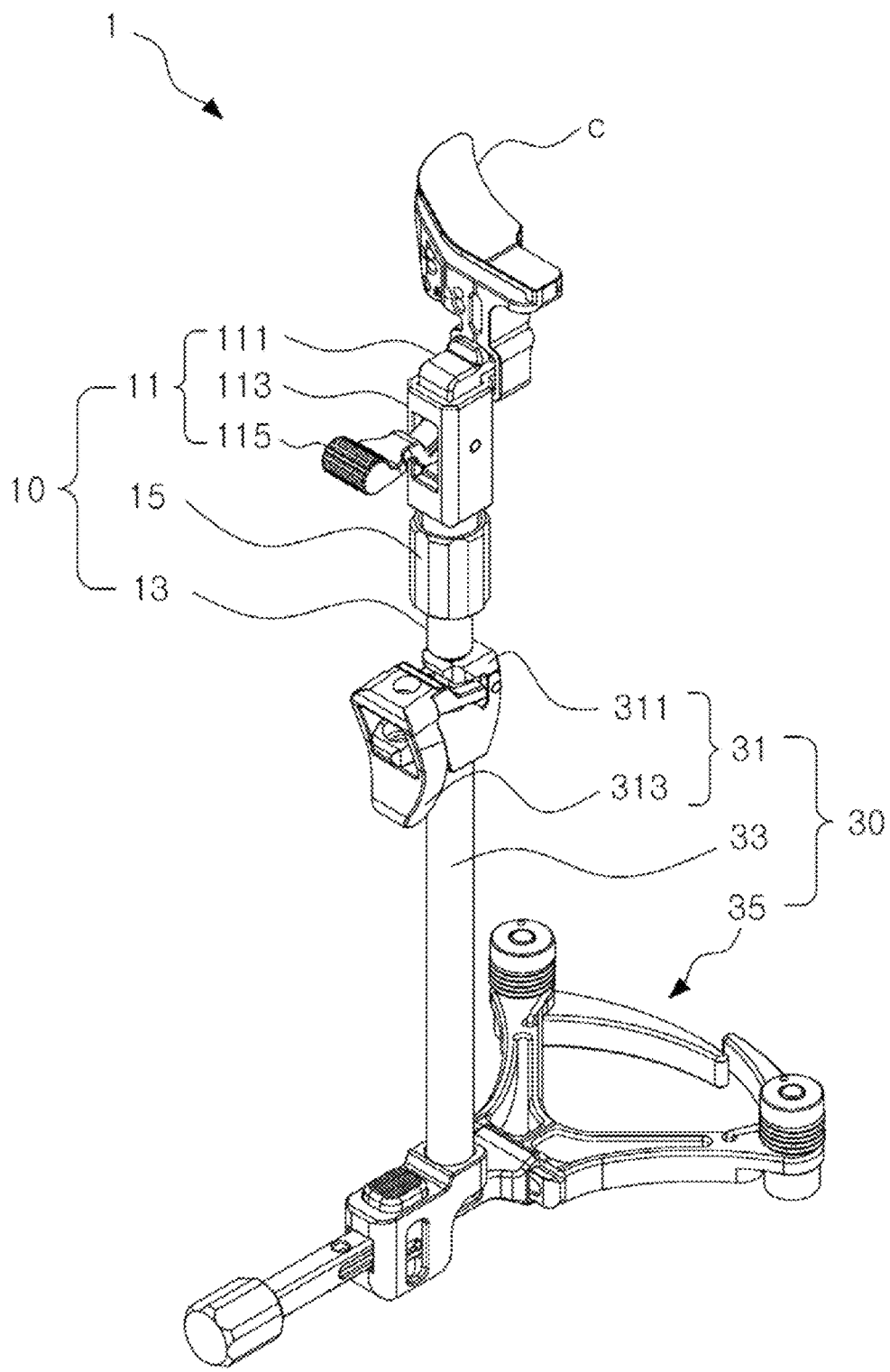
FIG. 2 is a perspective view illustrating a tibial alignment device according to an embodiment of the present disclosure.
Figure 3:
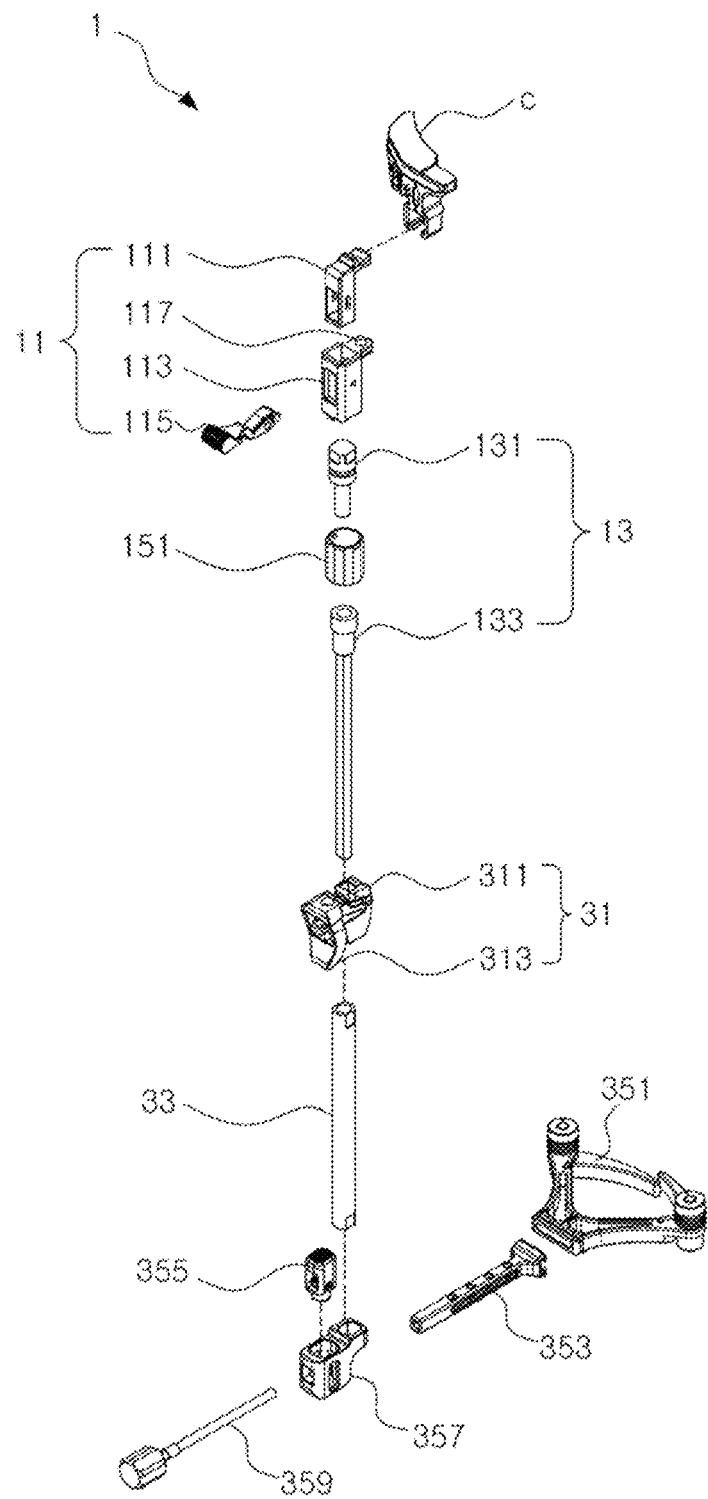
FIG. 3 is an exploded perspective view illustrating a tibial alignment device according to another embodiment of the present disclosure.

FIG. 2 is a perspective view illustrating a tibial alignment device according to an embodiment of the present disclosure, and FIG. 3 is an exploded perspective view illustrating a tibial alignment device according to another embodiment of the present disclosure.

Referring to FIGS. 2 and 3, a tibial alignment device 1 according to the present disclosure includes an upper part 10 capable of being coupled to a tibial cutting guide C for a total knee arthroplasty, and a lower part 30 capable of being coupled to the upper part 10 to be vertically slidable. In addition, the tibial alignment device 1 may further include a tibial cutting guide C for a tibial alignment device so as to form one unit.

As will be described later, the upper part 10 and the lower part 30 may include means for adjusting the coupling length therebetween in the middle thereof, and by adjusting the height of the device according to the length of the tibia of a subject to be treated, whereby information about an appropriate tibia cutting surface can be provided individually.

The upper part 10 is located close to the proximal tibia portion of the subject to be treated, and is coupled with the tibial cutting guide C so as to provide information on the reference of the accurate tibia proximal cutting surface. The upper part 10 may include a cutting guide coupling part 11, a connection part 13, and a fine adjustment part 15.

The cutting guide coupling part 11 is a part located at the upper end of the upper part 10 and coupled to the tibia cutting guide C, and is capable of being coupled to the tibia cutting guide C at various angles, as will be described below. Accordingly, it is possible to assure the safety and ease of a surgery procedure, and to prevent collision with other surgical instruments, thereby enabling an accurate surgery procedure. The cutting guide coupling part 11 may include a fastening member 111, a reception member 113, a lever member 115, and close contact means 117.

The connection part 13 has a cylindrical rod shape with an empty center. One end of the connection part 13 is coupled to the lower part 30 of the cutting guide coupling part 11 and the other end is received in the connection part 33 of the lower part 30 to be described later so as to support the tibial alignment device 1 and to provide a length that extends during height extension. Preferably, the connection part 13 includes an upper rod 131 and a lower rod 133 so that the length between the two rods can be finely adjusted through the fine adjustment unit 15 to be described later, thereby enabling a precise surgery procedure.

The fine adjustment part 15 can be coupled to the connection part 13, and it is possible to enable a precise surgery procedure by adjusting the coupling length between the upper rod 131 and the lower rod 133 to be described later so that fine height adjustment can be performed not only before the fixing of the tibial alignment device 1, but also after the fixing of the tibial alignment device 1. Preferably, the fine adjustment part 15 may further include a micro-knob 151, which will be described later.

The lower part 30 is located close to the distal tibia portion of a subject to be treated, and is slidably coupled with the upper part 10 so as to fix the tibial alignment device 1 to the ankle of the subject to be treated, which makes it possible to obtain accurate information on a cutting surface. The lower part 30 may include a height adjustment part 31, a connection part, and an ankle forceps part 35.

The height adjustment part 31 may be provided in the form of a metal housing, which receives the connection parts 13 and 33 of the upper part 10 and lower part 30 between the upper part 10 and the lower part 30. The height adjustment part 31 may include a button at one end for determining whether to extend the device, and allows the entire height of the tibial alignment device 1 to be adjusted by adjusting the coupling length of the upper part 10 and the lower part 30 while connecting the upper part 10 and the lower part 30. The height adjustment part 31 may include a first member 311, a second member 313, and an elastic member 315 to be described later.

The connection part 33 of the lower part 30 is made of a long cylindrical metal rod to form an empty space therein, whereby the connection part 33 of the lower part 30 is capable of receiving therein the connection part 13 of the upper part 10 while connecting the height adjustment part 31 and the ankle forceps part 35 to each other. Through this, it is possible to secure the entire height of the device and to adjust the height. Preferably, the connection part 33 of the lower part 30 may include, at opposite ends thereof, locking steps 331, which limit the coupling depths with the height adjustment part 31 and the ankle forceps part 35.

The ankle forceps part 35 has a shape of a hook or tongs including sickle-shaped members at opposite ends of a Y-shaped upper portion of a Y-shaped body so that the ankle forceps part 35 can be stably fixed to an ankle of a subject to be treated so that accurate information on the location of the tibia cutting surface can be known. The ankle forceps part 35 may include an ankle forceps 351, an ankle forceps connection part 353, a rachet button 355, a sliding adjustment part 357, and a connection bolt 359, which will be described later.

Figure 4:
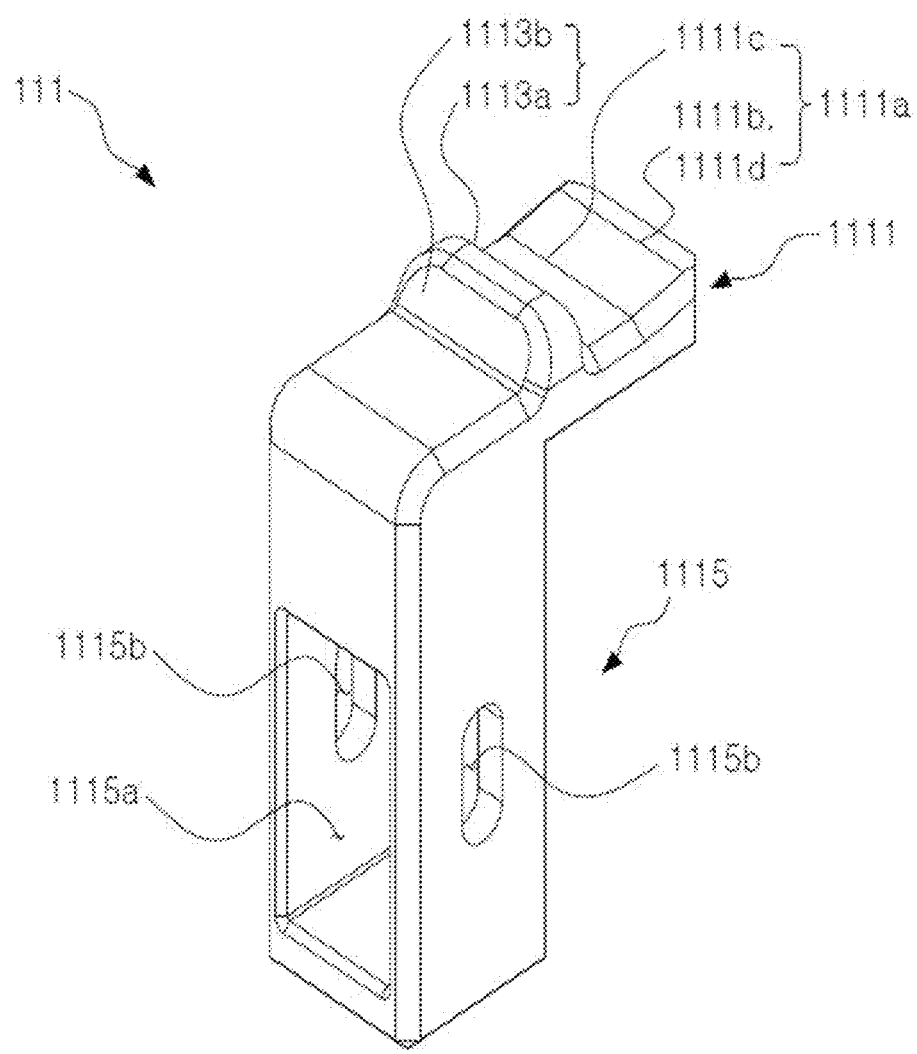
FIG. 4 is a perspective view illustrating a fastening member of a tibial alignment device according to another embodiment of the present disclosure.
Figure 5:
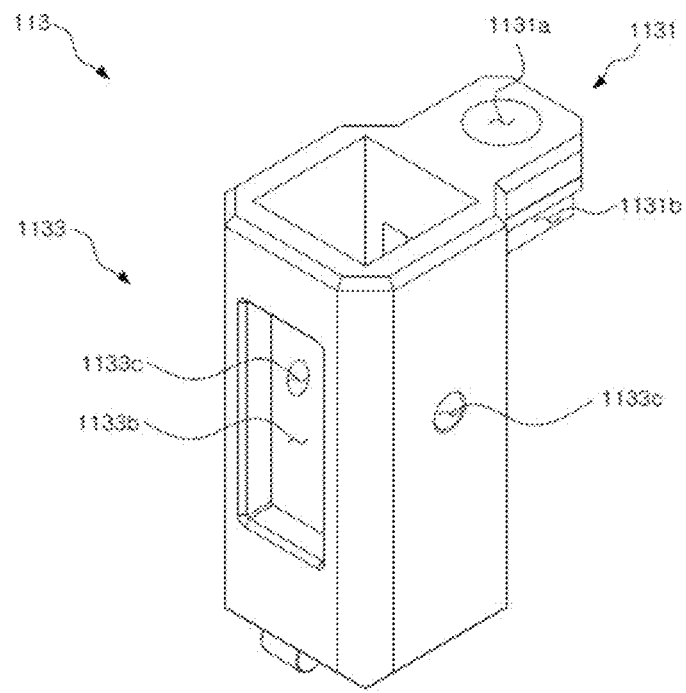
FIG. 5 is a perspective view illustrating a reception member of a tibial alignment device according to another embodiment of the present disclosure.
Figure 6:
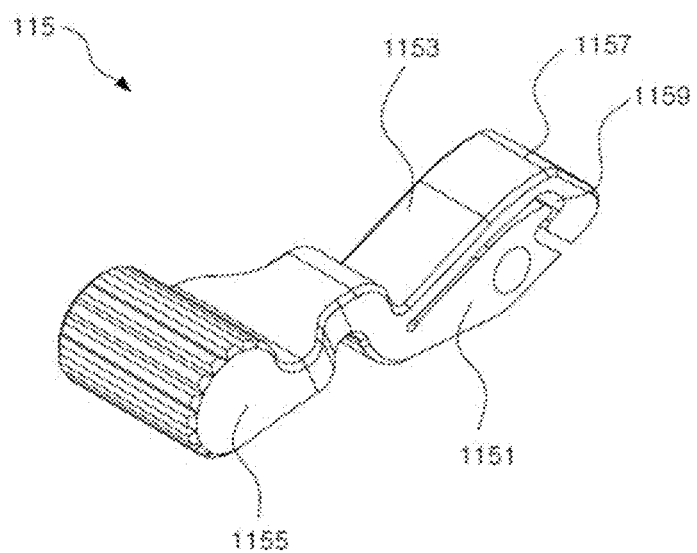
FIG. 6 is a perspective view illustrating a lever member of a tibial alignment device according to another embodiment of the present disclosure.
Figure 7:
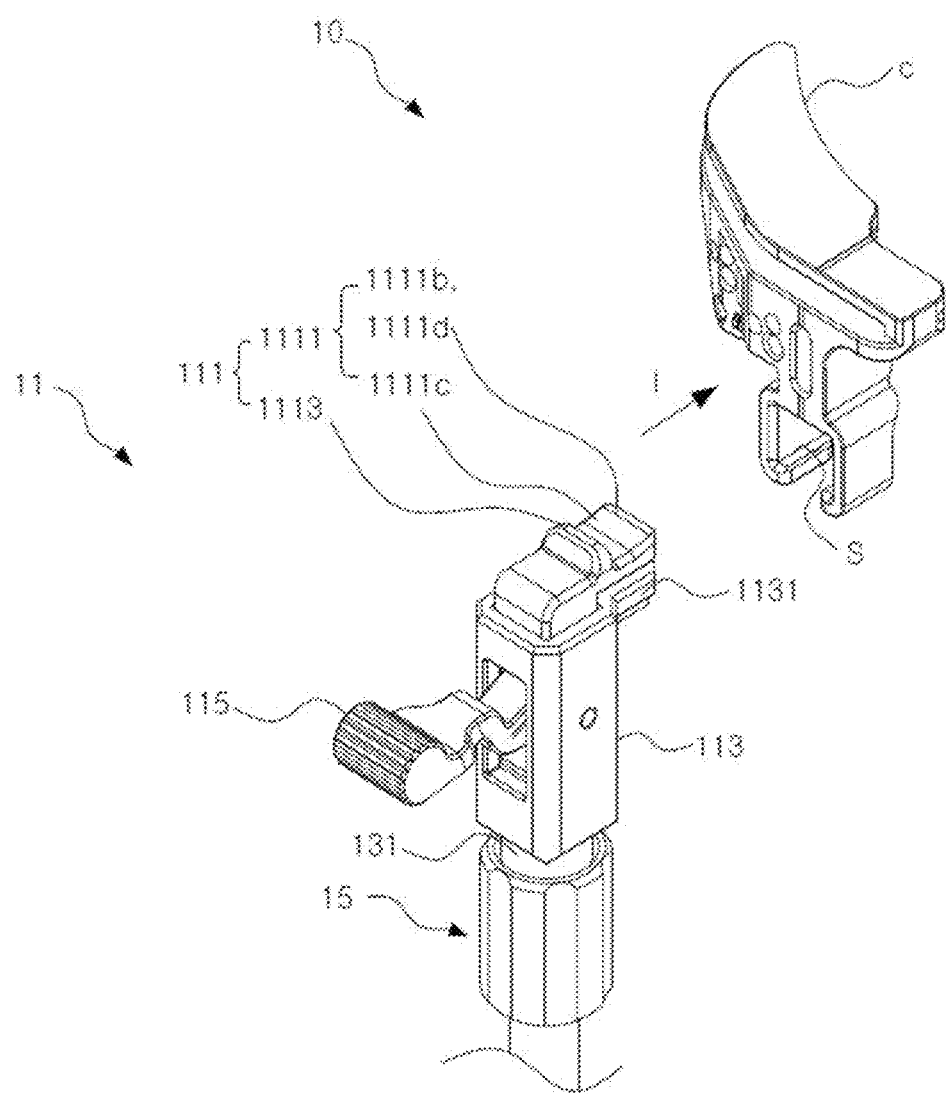
FIG. 7 is a perspective view illustrating an upper part of a tibial alignment device according to another embodiment of the present disclosure.

FIG. 4 is a perspective view illustrating a fastening member of a tibial alignment device according to another embodiment of the present disclosure, FIG. 5 is a perspective view illustrating a reception member of a tibial alignment device according to another embodiment of the present disclosure, FIG. 6 is a perspective view illustrating a lever member of a tibial alignment device according to another embodiment of the present disclosure, and FIG. 7 is a perspective view illustrating an upper part of a tibial alignment device according to another embodiment of the present disclosure.

Referring to FIGS. 4 to 7, the upper part 10 may include a cutting guide coupling part 11, a connection part 13, and a fine adjustment part 15, and the cutting guide coupling part 11 may include a fastening member 111, a reception member 113, a lever member 115, and close contact means 117.

As illustrated in FIG. 4, the fastening member 111 may be made of a metal and may have a shape in which an empty space for receiving the lever member 115 is formed in the shape of a short square bar, the center of which is bent. One end of the fastening member 111 is inserted into the tibia cutting guide C to secure a predetermined fixing force, and the other end is inserted into the inside of the reception member 113 provided in the form of a housing and is coupled to the reception member 113 so as to be movable vertically, which makes it possible to switch between the locked state and the unlocked state, which will be described later. The fastening member 111 may include a coupling part 1111, a stopper 1113, and a body part 1115, which will be described later.

The coupling part 1111 of the fastening member 111 protrudes in the insertion direction of the cutting guide coupling part 11 in an "L" shape at the upper end of the body part 1115 of the fastening member 111 so that the coupling part 1111 can be inserted and coupled to the tibia cutting guide C. As illustrated in FIG. 7, the coupling part 1111 is configured such that the gap between the coupling part 1111 and the coupling part 1131 of the reception member 113 to be described later is adjustable so as to allow the coupling part 1111 to be coupled and disassembled at various angles with respect to the tibial cutting guide C. Preferably, the coupling part 1111 may have a coupling surface 1111a including a protruding surface 1111b, one end of which protrudes upward, in order to firmly couple the coupling portion 1111 and to prevent separation in the direction opposite to the insertion direction after insertion and fixing. More preferably, the coupling surface 1111a may be configured as a curved surface to facilitate insertion and removal of the coupling part 1111. More preferably, as illustrated in FIGS. 4 to 8, the coupling surface 1111a may include a concave surface 1111c recessed into the inside of the coupling part 1111 and a convex surface 1111d extending from the concave surface and protruding to the outside of the coupling part 1111.

The concave surface 1111c is formed in the upper coupling surface 1111a of the engaging portion 1111 in an inwardly recessed shape. Thus, when the cutting guide coupling part 11 and the tibia cutting guide C are coupled or disassembled, the coupling part 1111 of the fastening member 111 can be smoothly inserted or separated without being caught on the outer corner of the coupling slot S in the tibia cutting guide C.

The convex surface 1111d is a configuration for preventing the separation of the cutting guide coupling part 11 by protruding upward in the shape of a curved surface at the insertion direction end of the fastening member coupling part 1111 such that after the cutting guide coupling part 11 and the tibia cutting guide C are coupled, the convex portion of the convex surface 1111d is engaged with the top surface of the coupling slot S in the tibial cutting guide C having a predetermined inclination. The convex surface 1111d may constitute the convex surface 1111b.

The stopper 1113 is formed to protrude outward from the upper end of the fastening member 111 at a position where the coupling part 1111 can be inserted to an appropriate depth to be in close contact with the coupling slot S in the tibial cutting guide C so as to be firmly fixed. The insertion depth of the coupling part 1111 can be limited. Preferably, for the safety of an operator and a subject to be treated, the corner portions of the stopper 1113 may be rounded. More preferably, the front surface of the stopper 1113 is formed as a vertical surface 1113a in order to secure a fixing force through close contact with the tibial cutting guide C, and the rear surface of the stopper 1113 may be formed as an inclined surface 1113b in order to ensure safe operation of the device and to prevent locking during a surgery procedure.

The body part 1115 is a configuration forming a body in the vertical direction of the L-shaped fastening member 111, and may include a lever member reception hole 1115a and a rotation coupling hole 1115b.

The lever member reception hole 1115a is a square empty space that penetrates the inside of the body part 1115 of the fastening member 111 in the insertion and separation direction I of the cutting guide insertion part 11 so as to receive the lever member 115, and provides a space in which the lever member 115 rotates so as to push up the top surface of the lever member reception hole 1115a.

The rotation coupling hole 1115b is a space penetrated in a horizontal direction perpendicular to the insertion and separation direction I of the cutting guide insertion part 11 in the body part 1115 of the fastening member 111, and is a configuration hinged with the rotating body part 1151 of the lever member 115. The rotation coupling hole 1115b may be formed as a groove having a vertically long shape in order to secure the moving range of the fastening member 111, which moves up and down.

As illustrated in FIG. 5, the reception member 113 may be configured as a short square rod-shaped housing having open top and bottom surfaces. Inside the housing shape, a hole for receiving the fastening member 111, the connection part 13, and the lever member 115, and a hole for hinge coupling may be formed in the side surface of the housing shape. The reception member 113 is coupled to the fastening member 111 so as to be slidable vertically. As will be described later, by adjusting the distance between the fastening member 111 and the coupling part 1131 of the reception member 113, it is possible to couple and disassemble the tibia alignment device 1 at various angles, as illustrated in FIG. 7, and to secure a firm fixing force when the tibia alignment device 1 is coupled. The reception member 113 may include a coupling part 1131 and a body part 1133, which will be described later.

The coupling part 1131 of the reception member 113 is formed at the upper end of one side surface of the reception member 113 to protrude in the insertion direction of the coupling portion of the cutting guide in a "¬" shape, so the coupling part 1131 is capable of being coupled to the tibia cutting guide C. Preferably, the coupling part 1131 of the reception member 113 may include, on the top surface thereof, a close contact means 117 for fixing the fastening member 111 to the reception member 113. More preferably, a magnet reception groove 1131a for receiving the close contact means 117 may be further included in the top surface of the coupling part 1131 of the reception member 113, which comes into contact with the bottom surface of the coupling part 1111 of the fastening member 111. More preferably, in order to firmly fix the tibial cutting guide C, the coupling part 1131 has a T-shaped cross section, and may include, in a corner portion of the bottom surface thereof, a guide groove 1131b recessed to the inside of the coupling part 1131.

The body part 1133 is a part constituting the body of the reception member 113 and has a shape of a hollow housing as described above to receive the fastening member 111 such that the fastening member 111 is vertically movable. The body part 1133 of the reception member 113 may further include a fastening member reception hole 1133a, a lever member reception hole 1133b, and a hinge coupling hole 1133c.

The fastening member reception hole 1133a is a square empty space formed by vertically penetrating the inside of the body part 1133 of the reception member 113, the body part 1115 of the fastening member 111 may be received in and coupled to the upper end of the fastening member reception hole 1133a to be vertically movable, and one end of the upper rod 131 of the connection part 13 may be inserted into and connected to the lower end of the fastening member reception hole 1133a.

The lever member reception hole 1133b is a square empty space that penetrates the inside of the body part 1133 of the reception member 113 in the insertion and separation direction I of the cutting guide insertion part 11 so as to receive the lever member 115, and provides a space in which the lever member 115 rotates so as to push up the top surface of the lever member reception hole 1115a.

The hinge coupling hole 1133c is a hole penetrated in a horizontal direction perpendicular to the insertion and separation direction I of the cutting guide insertion part 11 in the body part 1133 of the reception member 113, and may be hinged with the rotating body part 1151 of the lever member 115 so as to provide an axis for rotation of the lever member 1115.

As illustrated in FIG. 6, the lever member 115 is a configuration for adjusting the gap between the coupling part 1111 of the fastening member 111 and the coupling part 1131 of the reception member 113, and may include a rotating body part 1151, a leaf spring part 1153, a handle part 1155, a rotation prevention step 1157, and a groove 1159, which will be described later.

In the rotating body 1151, a cylindrical pin connecting the lever member 115 and the reception member 113 is inserted into and fixed in an empty hole penetrating the center of the lever member 115 so as to form a hinged coupling with the reception member 113, whereby the lever member 115 can rotate with respect to the reception member 113.

The leaf spring part 1153 is a plate-shaped elastic member 315 that surrounds the upper end of the lever member 115 and maintains a predetermined distance from the lever member 115, and when the lever member 115 rotates, the leaf spring part 1153 is retracted to the inside of the lever member so as to enable easy rotation of the lever member 115, and in the locked state to be described later, the leaf spring part 1153 presses the fastening member 111 upward so as to provide a coupling force between the cutting guide coupling part 11 and the tibial cutting guide C. Preferably, the top surface of the leaf spring part 1153 may be formed in a curved surface to facilitate the rotation of the lever member 115.

The handle part 1155 extends outward from the lever member 115 to allow an operator to rotate the lever member 115 with a small force, thereby allowing the operator to easily adjust the locked state and the unlocked state of the lever member 115. Preferably, a groove is formed in the outer circumferential surface of an end of the handle part 1155 so as to prevent a finger from slipping during manipulation by the operator, thereby enabling stable operation of the handle part 1155.

The rotation prevention step 1157 protrudes outward from the lever member 115 at a predetermined point in the leaf spring part 1153, so that when the operator does not manipulate the lever member 115, the rotation prevention step 1157 serves as a locking step that prevents rotation of the lever member 115 by the restoration force or elastic force of the leaf spring part 1153, thereby fixing the lever member 115 placed in a locked state to be described later so as to enable a safe surgery procedure.

Figure 11:
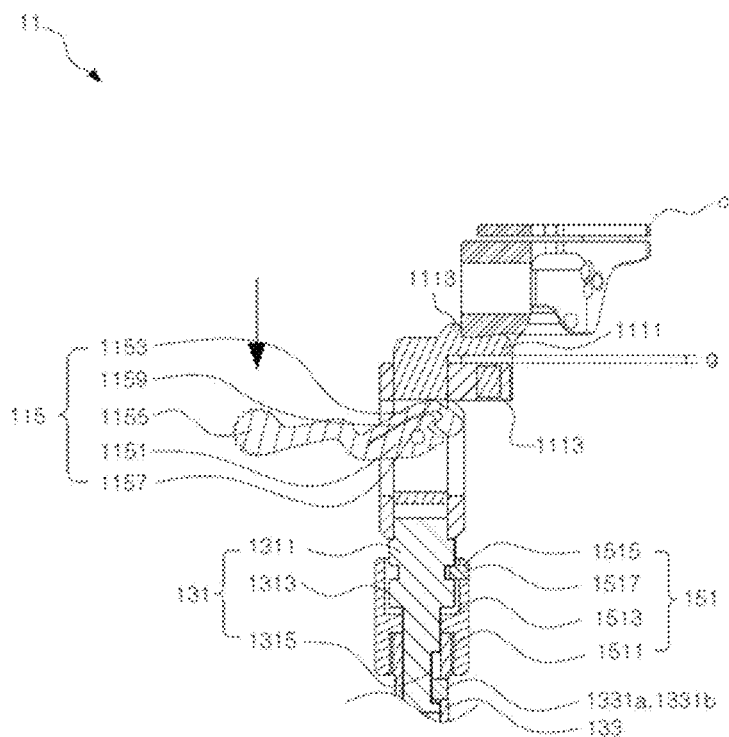
FIG. 11 is a cross-sectional view illustrating an upper part of a tibial alignment device according to another embodiment of the present disclosure after assembly.

The groove 1159 is a long groove formed between the leaf spring part 1153 and the rotation body part 1151, and may form a constant gap between the leaf spring part 1153 and the rotating body part 1151. As illustrated in FIG. 11, when the operator manipulates the handle part 1155 downward, the leaf spring part 1153 presses the fastening member 111 upward, so that the upper portion of the leaf spring part 1153 is engaged with on the top surface of the lever member reception hole 1115a, thereby limiting the rotation of the handle part 1155. The groove 1159 provides a predetermined space for allowing the leaf spring part 1153 to move downward, thereby facilitating the rotation of the lever member 115. Accordingly, the width of the groove 1159 is increased when the cutting guide coupling part 11 to be described later is in the unlocked state, and is decreased when the cutting guide coupling part 11 is in the locked state.

The close contact means 117 is preferably constituted with a magnet, is inserted into a magnet reception groove 1131a in the coupling part 1131 of the reception member 113, and is capable of naturally tightening the gap between the coupling parts 1111 and 1131 in the state in which the cutting guide coupling part 11 to be described later is unlocked without needing to apply a separate force.

Figure 8:
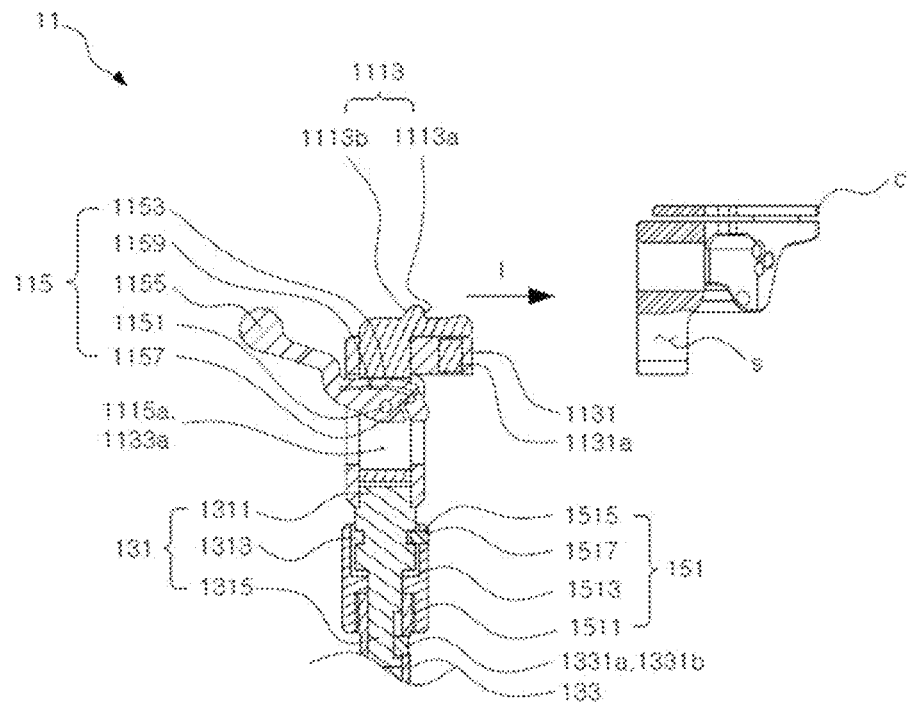
FIG. 8 is a cross-sectional view illustrating an upper part of a tibial alignment device according to another embodiment of the present disclosure before assembly.
Figure 9:
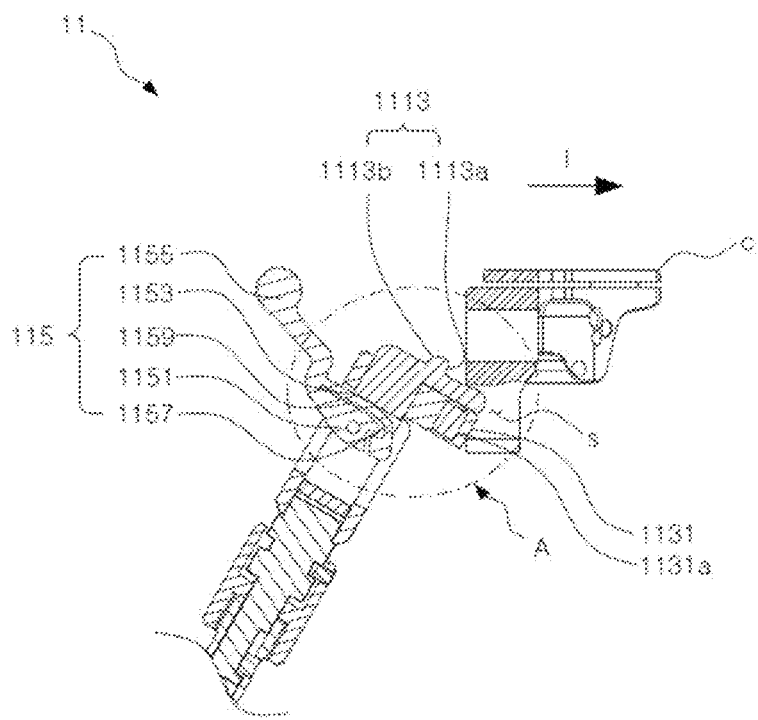
FIG. 9 is a cross-sectional view illustrating an upper part of a tibial alignment device according to another embodiment of the present disclosure in the process of assembly.
Figure 10:
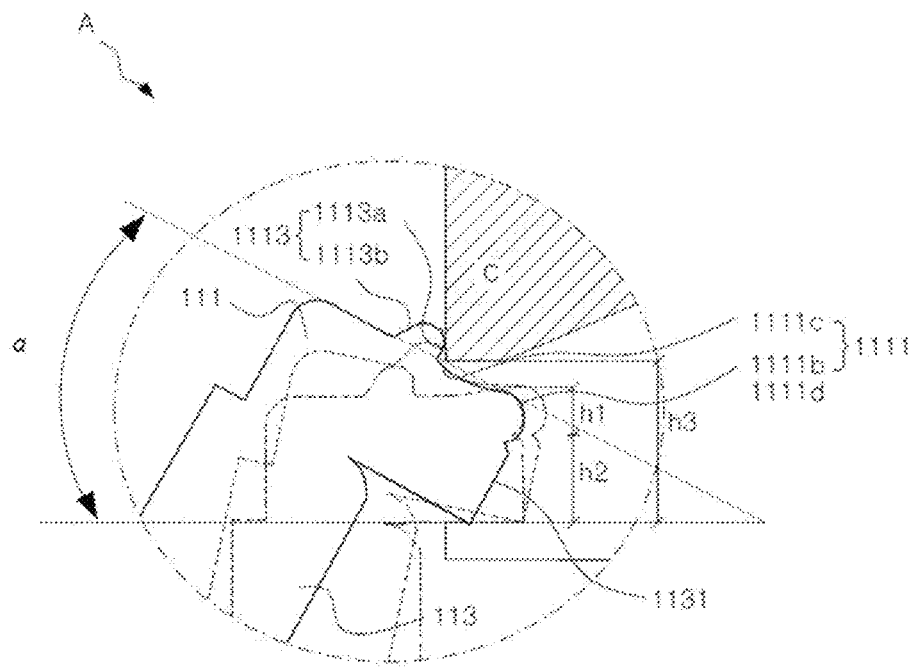
FIG. 10 is a view illustrating part A in FIG. 9 in detail.

FIG. 8 is a cross-sectional view illustrating an upper part of a tibial alignment device according to another embodiment of the present disclosure before assembly, FIG. 9 is a cross-sectional view illustrating an upper part of a tibial alignment device according to another embodiment of the present disclosure in the process of assembly, FIG. 10 is a view illustrating part A in FIG. 9 in detail, and FIG. 11 is a cross-sectional view illustrating an upper part of a tibial alignment device according to another embodiment of the present disclosure after assembly.

Hereinafter, a connective relationship between the above-described members and a coupling process and a disassembly process of the cutting guide coupling part 11 will be described. As illustrated in FIG. 7, the fastening member 111 is slidably coupled to the upper end of the fastening member reception hole 1133a in the reception member 113, the upper rod 131 of the connection part 13 is connected to the lower end of the fastening member reception hole 1133a in the reception member 113, and the rotatable lever member 115 is inserted into the lever member reception holes 1115a and 1133b formed inside the fastening member 111 and the reception member 113 and is rotatably fixed, whereby the cutting guide coupling part 11 may be configured.

First, an assembly process performed in the order of FIGS. 8, 9, and 11 will be described. Before the tibial alignment device 1 and the tibial cutting guide C are coupled to each other, as illustrated in FIG. 8, the fastening member 111 is received inside the reception member 113, and is fixed at the bottom side thereof by the close contact means 117 or the magnet provided on the top surface of the coupling part 1131 of the reception member 113. Accordingly, the gap between the coupling part 1111 of the fastening member 111 and the coupling part 1131 of the receiving member 113 is tightened.

Referring to FIGS. 9 and 10, the operate inserts the coupling parts 1111 and 1131 into the coupling slot S in the tibial cutting guide C in the state in which the gap between the coupling parts 1111 and 1131 is tightened by the close contact means 117 as described above. As illustrated in FIG. 10, in order to allow the operator to easily insert and separate the coupling parts into and from the coupling slot at various angles α during the coupling process, the height h of the inner space C1 at which the tibial cutting guide C receives the coupling part 1111 of the fastening member 111 and the coupling part 1131 of the reception member 113 may be larger than the sum h1+h2 of the height h1 of the coupling part 1111 of the fastening member 111 and the height h2 of the coupling part 1131 of the reception member 1113, and may be smaller than a height h3 in which the coupling part 1111 of the fastening part 111 is maximally raised upward when the lever member 115 is operated downward. Accordingly, when the cutting guide coupling part 11 and the tibial cutting guide C are coupled to each other or disassembled from each other, the operator may be provided with a wide coupling and disassembly radius α, thereby ensuring convenience and safety of the surgery procedure.

Next, referring to FIG. 11, when the operator inserts the coupling part 1111 of the fastening member 111 and the coupling part 1131 of the reception member 113 into the coupling slot S in the tibial cutting guide C and then rotates the lever member 115 downward, the leaf spring part 1153 presses the fastening member 111 upward, and the fastening member 111 moves upward, whereby the gap g between the coupling part 1111 of the fastening member 111 and the coupling part 1131 of the reception member 113 is widened. Accordingly, the upper side of the coupling part 1111 of the fastening member 111 presses the top surface of the coupling slot S in the tibial cutting guide C, and the cutting guide coupling part 11 is in the locked state in which the cutting guide coupling part 11 is firmly fixed to the tibial cutting guide C.

In contrast, referring to the disassembly process performed in the order of FIGS. 11, 9, and 8, which is the reverse of that of the coupling process, when the operator rotates the handle part 1155 of the lever member 115 upward, the leaf spring part 1153 stops pressing the bottom surface of the fastening member 111, whereby the fastening member 111 moves down again, and the gap between the coupling parts 1111 and 1131 of the fastening member 111 and the reception member 113 is narrowed. Accordingly, the cutting guide coupling part 11 is placed in the unlocked state in which the operator is capable of easily separating the coupling parts 1111 and 1131 from the coupling slot S in the tibial cutting guide C. Even in this disassembly process, as in the above-described coupling process, a wide disassembly radius may be provided between the cutting guide coupling part 11 and the tibial cutting guide C. Thus, the coupling parts 1111 and 1131 of the fastening member 111 and the reception member 113 can be easily separated, and can be prevented from colliding with surrounding surgical instruments, whereby it is possible to secure the convenience and safety of the surgery procedure.

In other words, as the handle part 1155 of the lever member 115 is vertically operated, the cutting guide coupling part 11 may be placed in the locked state in which the gap between the coupling part 1111 of the fastening member 111 and the coupling part 1131 of the reception member 113 is widened and thus the coupling parts 1111 and 1113 are firmly coupled to the tibial cutting guide C, or may be placed in the unlocked state in which the gap between the coupling parts 1111 and 1131 is narrowed and the coupling parts 1111 and 1131 can be detached from and attached to the coupling slot S in the tibial cutting guide C at various angles. By coupling or separating the cutting guide coupling part 11 and the tibial cutting guide C through this simple operation, it is possible to improve the ease of the surgery procedure and to prevent collision with the surrounding surgical instruments, thereby enabling a safe and accurate surgery procedure.

Figure 12:
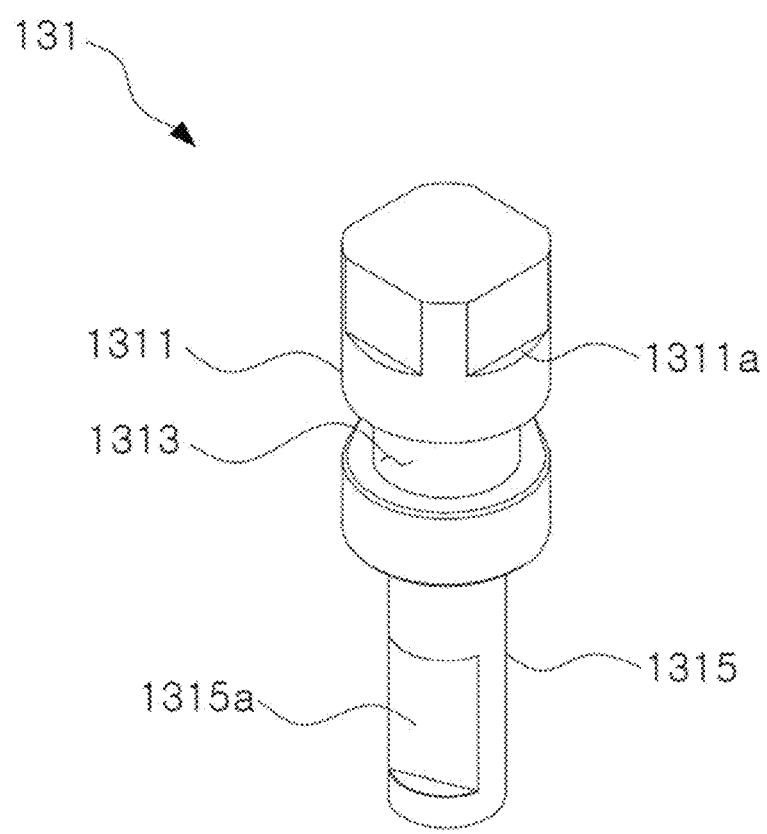
FIG. 12 is a perspective view illustrating an upper rod of a tibial alignment device according to another embodiment of the present disclosure.
Figure 13:
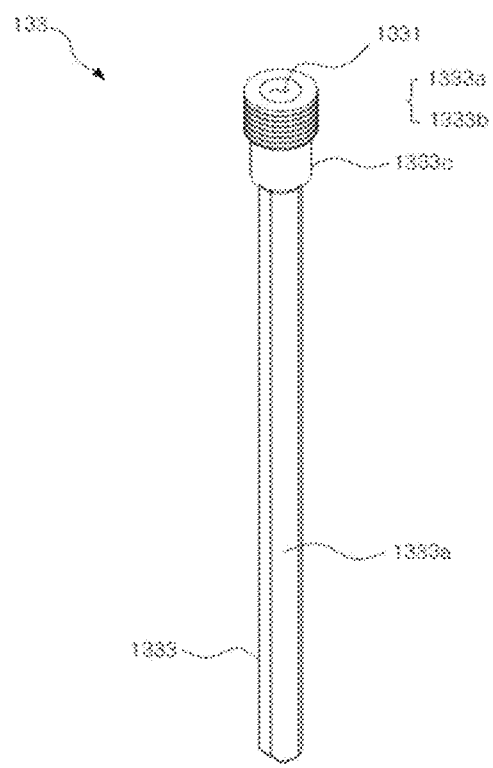
FIG. 13 is a perspective view illustrating a lower rod of a tibial alignment device according to another embodiment of the present disclosure.
Figure 14:
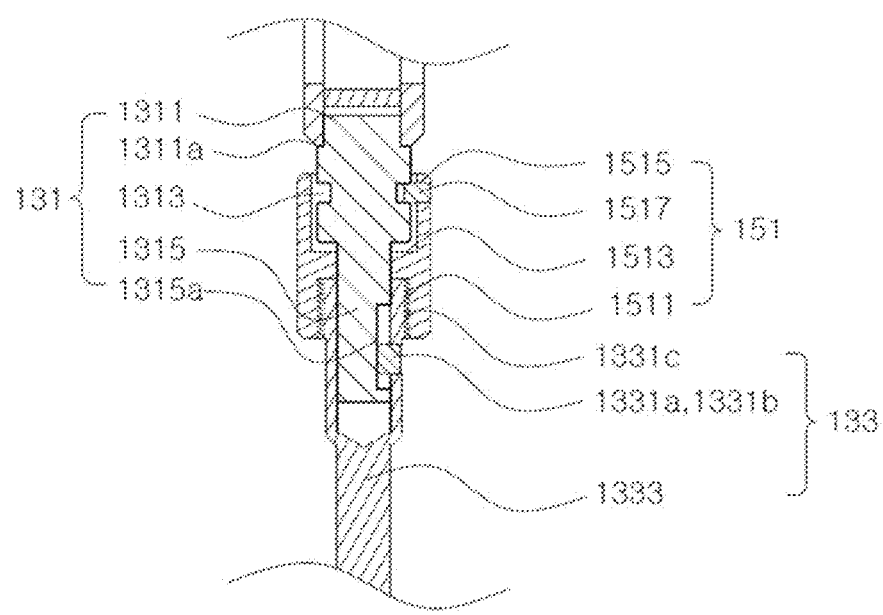
FIG. 14 is a cross-sectional view illustrating a fine adjustment part of a tibial alignment device according to another embodiment of the present disclosure.
Figure 15:
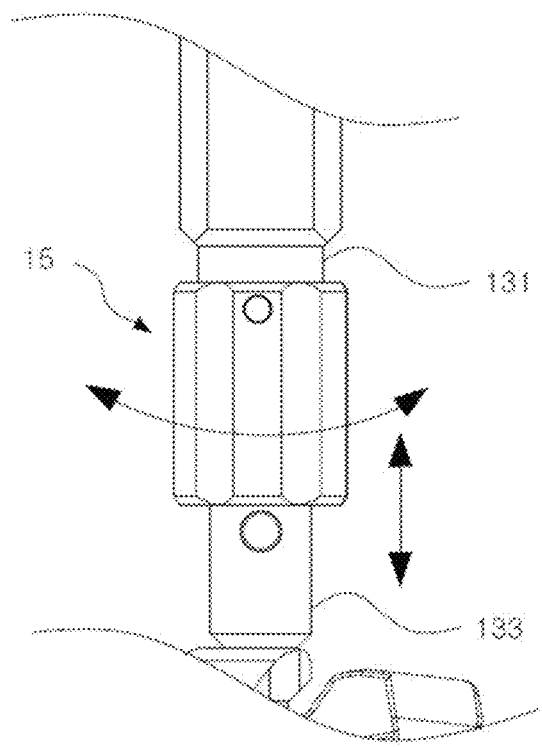
FIG. 15 is a view illustrating the use state of a fine adjustment part of a tibial alignment device according to another embodiment of the present disclosure.

FIG. 12 is a perspective view illustrating an upper rod of a tibial alignment device according to another embodiment of the present disclosure, FIG. 13 is a perspective view illustrating a lower rod of a tibial alignment device according to another embodiment of the present disclosure, FIG. 14 is a perspective view illustrating a fine adjustment part of a tibial alignment device according to another embodiment of the present disclosure, and FIG. 15 is a perspective view illustrating a use state a fine adjustment part of a tibial alignment device according to another embodiment of the present disclosure.

Referring to FIGS. 12 to 15, as described above, the connection part 13 may include an upper rod 131 and a lower rod 133, and the fine adjustment part 15 may include a micro-knob 151.

The upper rod 131 has a shape of a short cylindrical metal rod. One end of the upper rod 131 is formed as a square pillar suitable for the square shape of the lower end of the fastening member reception groove 1133a in the reception member 113 to be coupled to the reception member 113, and the other end of the upper rod 131 is formed as a cylindrical pillar suitable for the inner space of the lower rod 133 to be connected to the lower rod 133. The upper rod 131 may further include a reception member insertion part 1311, a pin groove 1313, and a lower rod insertion part 1315.

The reception member insertion part 1311 is formed in the shape of a square pillar, and is inserted into and fixed to the lower end of the fastening member reception groove 1133a in the reception member 113. Preferably, the reception member insertion part 1311 may include a circular locking step 1131 formed at the lower side thereof to surround the square pillar shape so as to adjust the coupling depth between the fastening member 111 and the upper rod 131.

The pin groove 1313 forms the periphery of the empty space surrounding the cylindrical pillar between one end and the other end of the upper rod 131, and may be engaged with a pin 1517 inserted into a pinhole 1515 in the micro-knob 151 so as to fix the position of the micro-knob 151 with respect to the upper rod 131 and to allow the micro-knob 151 to be movably coupled so as to be rotatable.

The lower rod insertion part 1315 is a cylindrical rod extending from the lower end of the upper rod 131, and according to the rotation of the micro-knob 151 to be described later, the lower rod insertion part 1315 may be inserted into the upper rod reception part 1331 of the lower rod 133 to be vertically slidable. Preferably, a sliding groove 1315a recessed in a "⊏" shape is formed in the outer surface of the lower rod insertion part 1315 so as to limit the movement of the pin 1517 coupled to the pinhole 1331a in the lower rod 133 and hence the movement of the upper rod 131 when sliding over a predetermined range, thereby limiting the sliding range of the upper rod 131.

The lower rod 133 is formed of a long rod having a cylindrical shape, and may include an upper rod reception part 1331, which receives the upper rod 131, at one end, and a lower insertion part 1333, which is inserted into the height adjustment part 31 and the connection part 33 of the lower part 30, at the other end.

The upper rod reception part 1331 may have an empty inner space formed at the upper end of the lower rod 133 to receive the lower rod insertion part 1315 of the upper rod 131. The upper rod reception part 1331 includes a pinhole 1331a penetrating the outer peripheral surface of the reception part 1331 of the lower rod 133. When the pin 1331b is inserted into the pinhole 1331a, the upper rod 131 and the lower rod 133 may be fixed, and the upper rod 131 and the lower rod 133 are vertically movable in a range provided in the sliding groove 1315a in the upper rod. In addition, by forming a thread 1331c on the outer circumferential surface of the reception part 1331 and causing the thread 1331c to be engaged with a thread 1511 of the micro-knob 151 to be described later, it is possible to perform an accurate surgery procedure by finely adjusting the length of the upper part 10.

The lower insertion part 1333 is a thin cylindrical rod, and is inserted through the height adjustment part 31 and the connection part 33 of the lower part 30. Preferably, the outer surface of the insertion part 1333 may further include a sliding surface 1333a to be in contact with a contact part 3135 to be described later along the height in which the lower rod 133 vertically sides.

As described above, the fine adjustment part 15 may include a micro-knob 151 capable of being pin-coupled to the pin groove 1313 in the connection part 13 of the upper part 10. Preferably, the micro-knob 151 may further include a thread 1511 and a locking step 1513 on an inner circumferential surface, as illustrated in FIG. 14. More preferably, the micro-knob 151 may further include a pinhole 1515 formed at a position of the pin groove 1313 of the upper rod 131 at the upper side of the outer surface thereof, and by fixedly inserting a pin 1517 into the pinhole 1515, it is possible to fix the upper rod 131 and the micro-knob 151, and to make the micro-knob 151 rotatable at a predetermined position with respect to the upper rod 131. More preferably, irregularities may be formed on the outer circumferential surface of the micro-knob 151 so as to provide a frictional force when the operator rotates the micro-knob 151, thereby achieving accuracy and convenience of operation.

Hereinafter, the fine height adjustment of the tibial alignment device 1 through the manipulation of the fine adjustment part 151 will be described.

As illustrated in FIGS. 14 and 15, one end of the micro-knob 151 is movably coupled to the pin groove 1313 in the upper rod 131 to be rotatable through pin coupling, and the other end is connected to the lower rod 133 via a thread 1511 formed inside the micro-knob 151. The upper rod 131 and the lower rod 133 are fixed by being coupled to each other via a pin 1331b, and the pin 1517 inserted into the pinhole 1515 is brought into close contact with the surface of the sliding groove 1333a in the lower rod insertion part 1333, whereby the vertical sliding range can be limited and the upper rod 131 can be prevented from rotating together with the micro-knob 151 when the operator manipulates the micro-knob 151. Therefore, in the state in which the upper rod 131 and the lower rod 133 are stably fixed, the operator is capable of acquiring information on the accurate cutting surface by slowly rotating the micro-knob 151 and finely adjusting the height of the tibial alignment device 1.

Figure 16:
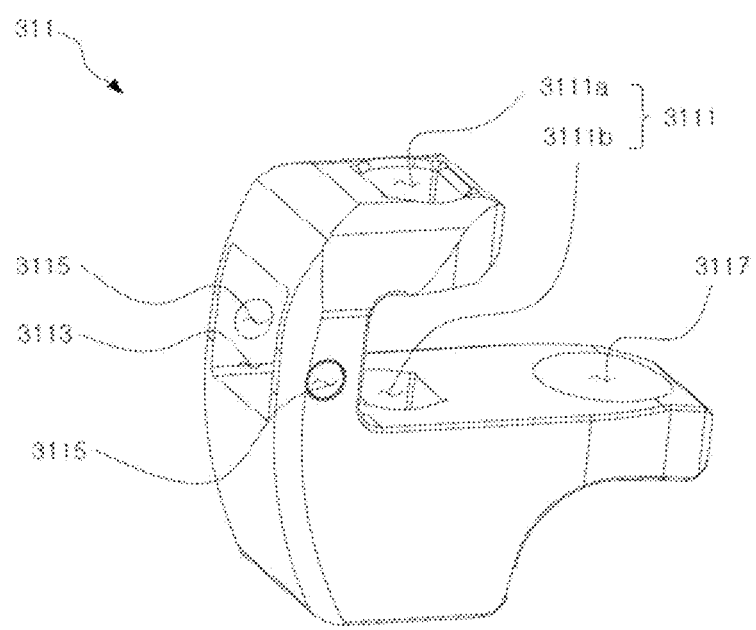
FIG. 16 is a perspective view illustrating a first member of a tibial alignment device according to another embodiment of the present disclosure.
Figure 17:
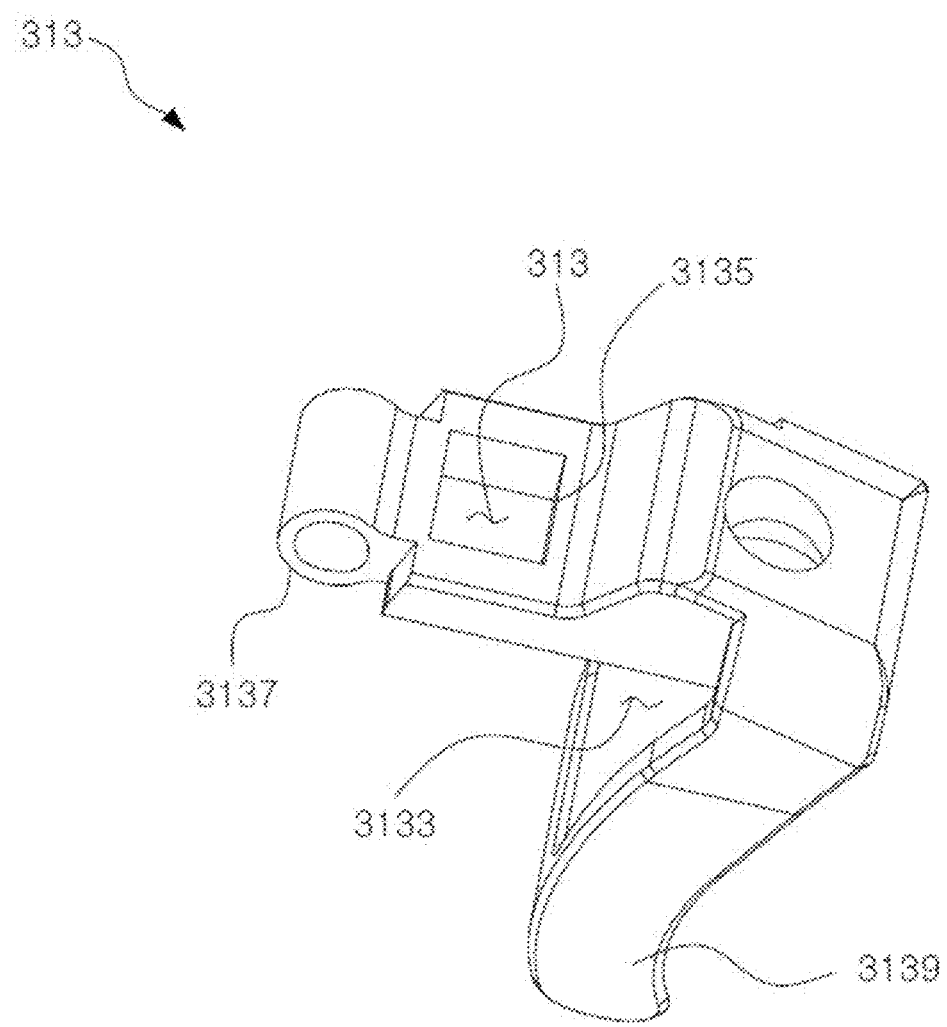
FIG. 17 is a perspective view illustrating a second member of a tibial alignment device according to another embodiment of the present disclosure.
Figure 18:
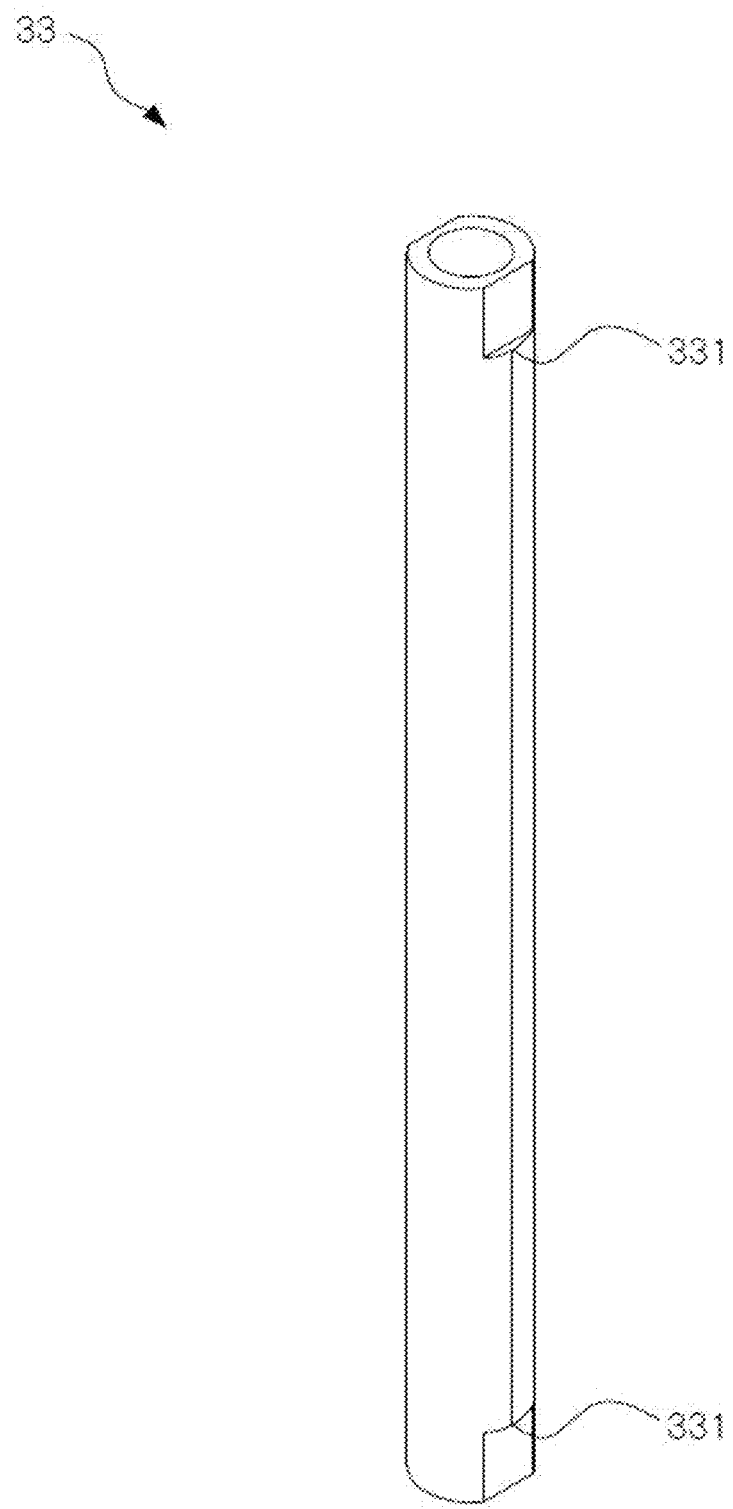
FIG. 18 is a perspective view illustrating a connection part of a tibial alignment device according to another embodiment of the present disclosure.
Figure 19:
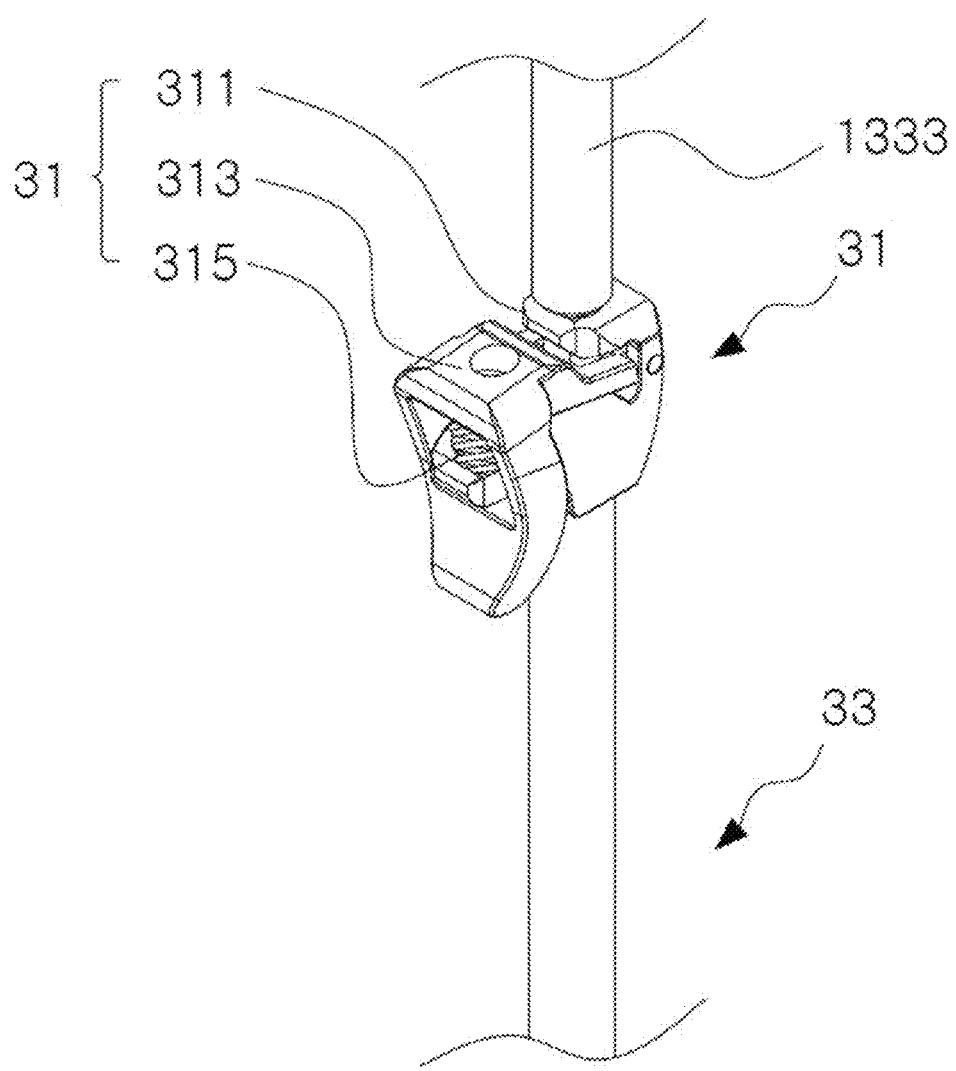
FIG. 19 is a perspective view illustrating a height adjustment part of a tibial alignment device according to another embodiment of the present disclosure.

FIG. 16 is a perspective view illustrating a first member of a tibial alignment device according to another embodiment of the present disclosure, FIG. 17 is a perspective view illustrating a second member of a tibial alignment device according to another embodiment of the present disclosure, FIG. 18 is a perspective view illustrating a connection part of a tibial alignment device according to another embodiment of the present disclosure, and FIG. 19 is a perspective view illustrating a height adjustment part of a tibial alignment device according to another embodiment of the present disclosure.

Referring to FIGS. 16 to 19, as described above, the lower part 30 may include a height adjustment part 31, a connection part 33, and an ankle forceps part 35, and the height adjustment part 31 may include a first member 311, a second member 313, and an elastic member 315.

As illustrated in FIG. 16, the first member 311 is a ⊏-shaped member having therein a vertical empty space through which the lower rod 133 of the upper part 133 passes, wherein the lower rod 133 of the upper part 10 is loosely connected to the upper side of the first member 311 to be vertically slidable, and the upper end of the connection part 33 of the lower part 30 is fixed to the lower side of the first member 311 so that the lower rod 133 of the upper part 10 can be received inside the connection part 33 of the lower part 30 while sliding downward. The first member 311 may further include a vertical through hole 3111, a horizontal through hole 3113, a rotation coupling hole 3115, and an elastic member reception groove 3117.

The vertical through hole 3111 is an empty space vertically penetrating the ⊏-shaped first member 311, and may include a first hole 3111a and a second hole 3111b penetrating the horizontal body of the ⊏-shaped first member.

The first hole 3111a is formed vertically through the upper end of the first member 311, and may receive the lower rod 133 of the upper part 10 such that the lower insertion part 1333 of the lower rod 133 of the upper part 10 is inserted into the upper side of the first hole 311 to be vertically slidable.

The second hole 3111b is formed vertically through the lower end of the first member 311 and has a space formed in a portion of the upper side thereof to slidably receive the lower rod 133 and an empty space formed in a portion of the lower side thereof to be coupled with the upper end of the connection part 33 of the lower part 30, whereby the lower rod 133 of the upper part 10 can be inserted through the inner space of the second hole 3111b and the upper end of the connection part 33 of the lower part 30 can be coupled to the lower end of the lower rod 133.

The horizontal through hole 3113 is an empty space horizontally penetrating the ⊏-shaped first member 311, and may receive an end of the second member 313 so that the rotation space for the second member 313 can be secured.

The rotation coupling hole 3115 is formed to pass through the body of the first member 311 in a direction orthogonal to the direction in which the horizontal through hole 3113 passes so that the rotation shaft of the rotation coupling part 3137 of the second member 313 can be received in the rotation coupling hole 3115.

The elastic member reception groove 3117 is formed in a shape recessed inward at the lower end of the "⊏" shape, and may receive and fix one end of the elastic member 315.

As illustrated in FIG. 17, the second member 313 is a member having ¬ shape, wherein, in the horizontal body of the ¬ shape, the vertical through hole 3131 may be formed to vertically penetrate the second member 313, and in the vertical body of the ¬ shape, the horizontal through hole 3133 may be formed to vertically penetrate the second member. The second member 313 may include a contact part 3135, a rotation coupling part 3137, and a handle part 3139.

The vertical through hole 3131 is formed as an empty space vertically penetrating the ¬-shaped second member 313, and may serve to receive the lower rod 133 of the upper part 10 therein.

The horizontal through hole 3133 is formed as an empty space horizontally penetrating the second member 313 of the ¬ shape, and may receive the lower part of the first member 311 of the ⊏ shape, thereby securing a radius of rotation of the second member.

The contact part 3135 is formed on the outer circumferential surface of the vertical through hole 3131 in the second member 313, and, when the second member 313 rotates, comes into contact with the lower rod of the upper part 10, thereby forming a frictional force. Thus, in the locked state described later, the contact part 3135 may serve to firmly fix the lower rod 133 of the upper part 10. Preferably, the contact part 3131 has a shape complementary to the contact surface of the lower rod 133 so that the contact part 3131 can be in stable contact with the lower rod 133 to fix the lower rod 133 and can maximize the frictional force generated through the contact.

The rotation coupling part 3137 is formed at the end of the upper part 10 of the ¬ shape forming the second member 313, and is partially inserted into the horizontal through hole 3113 in the first member 311 to be fixed, thereby making the second member 313 rotatable such that the gap between the contact part 3131 and the lower rod 133 of the upper part 10 can be adjusted.

The handle part 3139 is formed on the outer surface of the vertical member of the ¬ shape forming the second member 313 such that the operator can rotate the second member 313 by manipulating the second member 313. Preferably, the handle part 3135 may be formed such that the lower end is bent more to the outside toward the bottom for ease of operation.

As illustrated in FIG. 19, the elastic member 315 is located on the top surface of the horizontal through hole 3133 of the second member 313, and presses the second member 313 upward such that the second member 313 and the lower rod 133 of the upper part 10 are brought into contact with each other in the locked state to be described later, thereby fixing the lower rod 133 of the upper part 10 so as to enable a safe surgery procedure. Preferably, the elastic member 315 may be constituted with a spring.

The connection part 33 of the lower part 30 is a long hollow cylindrical pillar, wherein one end of the connection part 33 can be connected and fixed to the lower end of the first member 311, and the other end of the connection part 33 can be connected and fixed to the ankle forceps part 35 so that the lower rod 133 of the upper part 10, which vertically slides, can be received in the connection part 33. Preferably, the connection part 33 of the lower part 30 may further include, at opposite ends thereof, locking steps 331 for limiting the insertion depth and preventing rotation after fixing.

Figure 20:
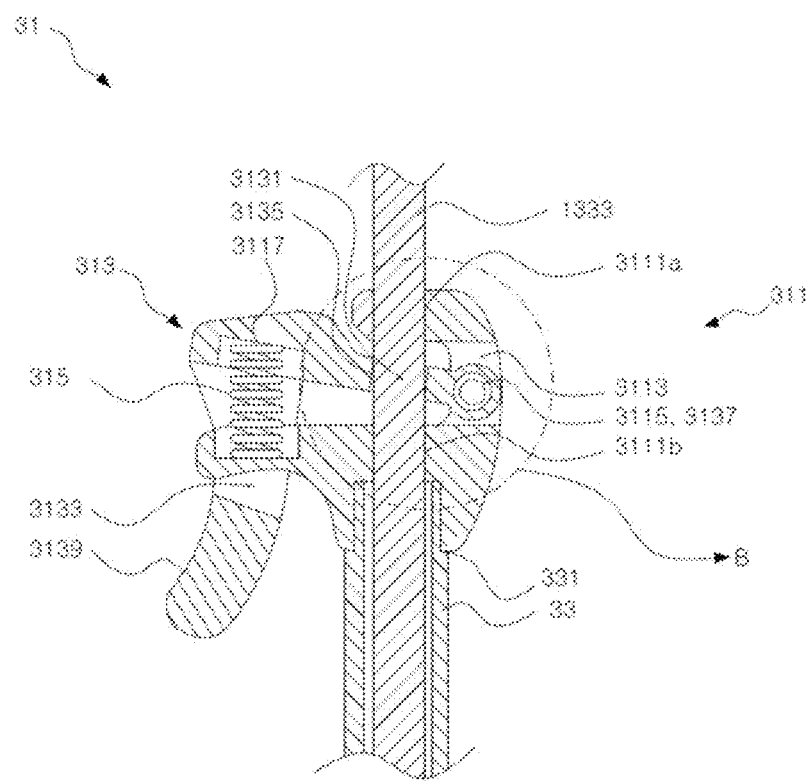
FIG. 20 is a cross-sectional view illustrating a height adjustment part of a tibial alignment device according to another embodiment of the present disclosure in the locked state.
Figure 21:
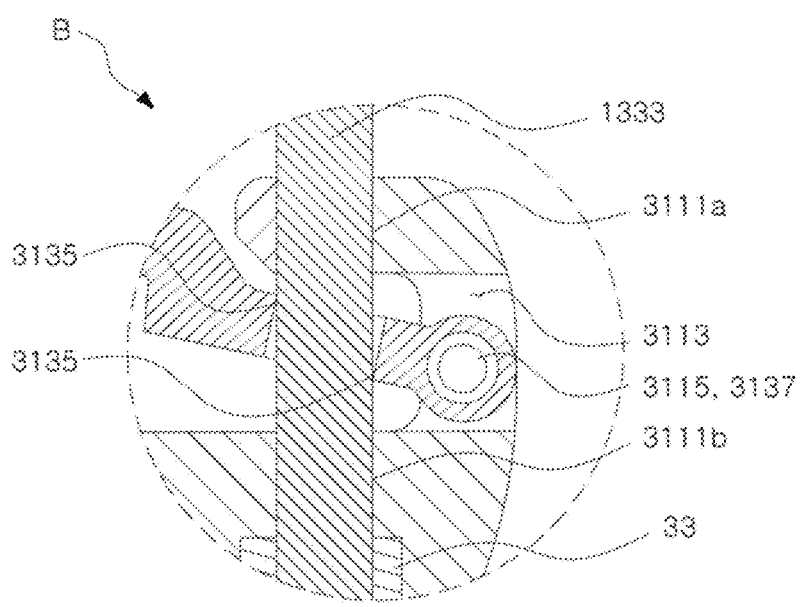
FIG. 21 is a view illustrating part B in FIG. 20 in detail.
Figure 22:
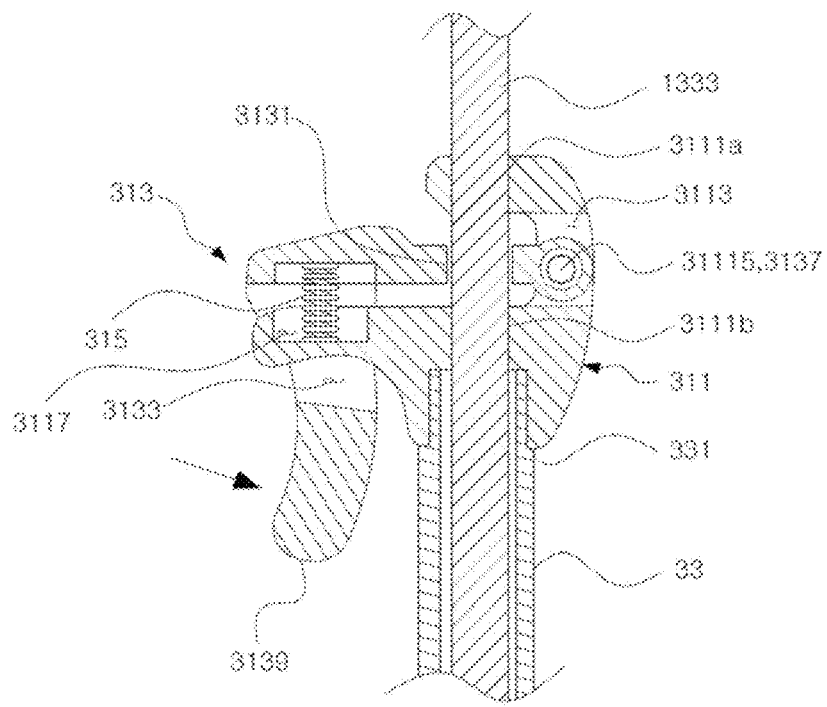
FIG. 22 is a cross-sectional view illustrating a height adjustment part of a tibial alignment device according to another embodiment of the present disclosure in the unlocked state.

FIG. 20 is a cross-sectional view illustrating a height adjustment part of a tibial alignment device according to another embodiment of the present disclosure in the locked state, FIG. 21 is a view illustrating part B in FIG. 20 in detail, and FIG. 22 is a cross-sectional view illustrating a height adjustment part of a tibial alignment device according to another embodiment of the present disclosure in the unlocked state.

Hereinafter, a process of adjusting the height of the height adjusting unit 31 will be described.

As described above, in the conventional device adopting a mechanism of a bolt or a rachet, there is a limitation in accurate positioning. However, the tibial alignment device 1 according to the present disclosure is capable of making it possible to enable accurate length adjustment and fixing by coming into contact with or being spaced apart from the connection part 13 of the upper part 10 that is slidable according to the rotation of the second member 313.

Referring to FIG. 22, when the operator manipulates the handle part 3139 at the lower end of the second member 313 downward, the contact part 3135 forms a gap with respect to the sliding surface 1333*a* of the lower rod 133 of the upper part 10, and the operator can adjust the overall height of the tibial alignment device 1 by vertically sliding the lower rod 133. In contrast, as illustrated in FIGS. 20 and 21, when the operator does not manipulate the handle part 3139, the second member 313 is pressed upward by the elastic member 315 so as to be rotated and fixed. As a result, the contact part 3131 comes into contact with the sliding surface 1333*a* of the lower rod 133 of the upper part 10 so that the lower rod 133 can be firmly fixed again. This process is performed through the simple manipulation of the handle part 3139, thereby enabling much easier height adjustment than the manipulation method using other screws or rackets.

In other words, according to the user's manipulation, the height adjustment part 31 of the tibial alignment device 1 according to the present disclosure may be placed in the locked state in which the lower rod 133 of the upper part 10 comes into contact with the contact part 3131 of the second member 313 to fix the lower rod 133, or in the unlocked state in which a gap is formed between the connection part 13 of the upper part 10 and the second member 313, thereby making the connection part 13 of the upper part 10 vertically slidable. The simple manipulation of the handle part 3139 enables easy switching between the locked state and the unlocked state, thereby promoting safety and convenience of surgery.

Figure 23:
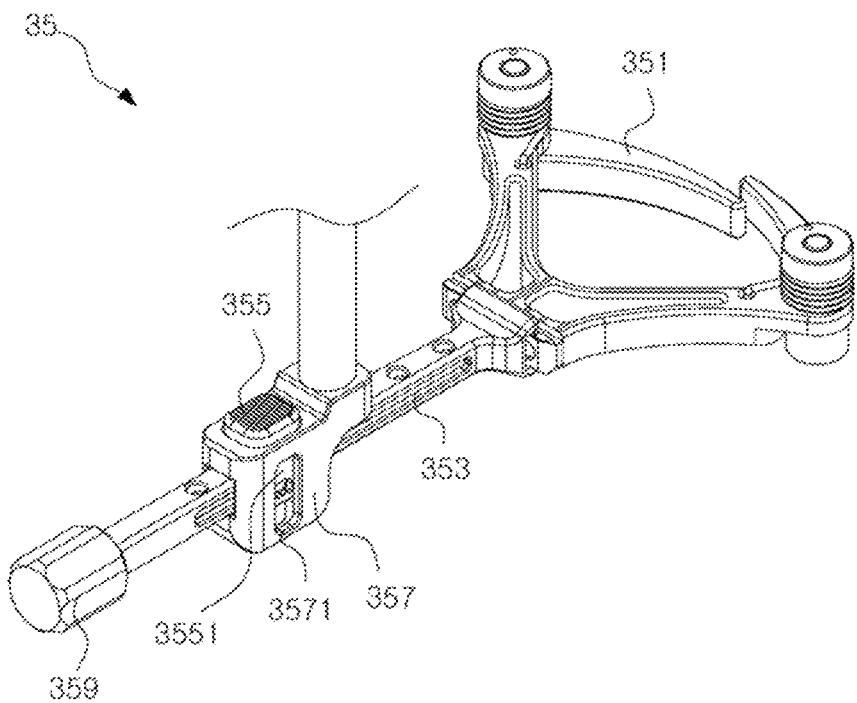
FIG. 23 is a perspective view illustrating an ankle forceps part of a tibial alignment device according to another embodiment of the present disclosure.

FIG. 23 is a perspective view illustrating an ankle forceps part 35 of a tibial alignment device according to another embodiment of the present disclosure.

Referring to FIG. 23, the ankle forceps part 35 may include an ankle forceps 351, an ankle forceps connection part 353, a rachet button 355, a sliding adjustment part 357, a connection bolt 359, and cleaning grooves 3551 and 3571.

The ankle forceps 351 has a shape similar to the upper portion of the Y shape of the ankle forceps part 35, and a hook-shaped member is rotatably attached to the end of the ankle forceps portion 35 so that the tibial alignment device 1 can be detached from or attached to an ankle of a subject to be treated.

The ankle forceps connection part 353 has a shape of a long rod penetrating the sliding adjustment part 357, wherein the ankle forceps 351 is connected to one end of the ankle forceps connection part 353 and the connection bolt 359 is coupled to the other end of the ankle forceps connection part 353 so as to connect the ankle forceps 351 to the tibial alignment device 1. The ankle forceps connection part 353 is capable of sliding in the anterior or posterior direction of the subject to be treated, and a toothed thread is formed on the bottom surface of ankle forceps connection part 353 to be engaged with a thread inside the rachet button 355 so as to move and fix the tibial alignment device 1 so that the coupling angle of the tibial alignment device 1 can be appropriately adjusted.

The rachet button 355 is a member of a square pillar in which an inner empty space is formed, and is inserted into a hole formed in the top surface of the sliding adjustment part 357, and a screw thread is formed on the bottom surface of the inner space so as to adjust whether to slide the forceps connection part 353. When the rachet button 355 is pressed down, a gap is formed between the ankle forceps connection part 353 and the rachet button 355 so that the ankle forceps connection part 353 can be slid in the anterior and posterior directions of the subject to be treated. When the rachet button 355 is not manipulated, the ankle forceps connection part 353 is firmly engaged with the rachet button 355 and the tibial alignment device 1 can be stably fixed. Preferably, the rachet button 355 may further include a cleaning groove 3551 penetrating opposite side surfaces of the lower end into which the connection bolt 359 is inserted in order to increase the cleaning efficiency of the device.

The sliding adjustment part 357 may be provided in the form of a housing surrounding the rachet button 355, the sliding connection part, and the connection bolt 359, wherein a vertical through hole for receiving the connection part 33 of the lower part 30 and the rachet button 355 may be formed in the upper end of the sliding adjustment part 357 and a horizontal through hole for receiving the connection bolt 359 may be formed in the side surface of the sliding adjustment part 357. Preferably, the sliding adjustment part 357 may further include cleaning grooves 371 for enhancing cleaning efficiency in both side surfaces into which the rachet button 355 is inserted.

The connection bolt 359 is in the shape of a long rod and has one end connected to the ankle forceps 351, and may be configured to horizontally penetrate the sliding adjustment part 357 and the rachet button 355 to connect and fix the sliding adjustment part 357 and the rachet button 355. Preferably, the one end of the connection bolt 359 is screwed with the ankle forceps 351, and the other end is provided with a knob for facilitating rotation so that the ankle forceps part 35 can be easily coupled to and disassembled from the tibial alignment device 1.

The foregoing detailed description exemplifies the present disclosure. In addition, the foregoing description is intended to illustrate and explain embodiments of the present disclosure, and the present disclosure may be used in various other combinations, modifications, and environments. That is, it is possible to change or modify the present disclosure within the scope of the concept of the present disclosure disclosed in this specification, within the scope equivalent to the above-described contents, and/or within the scope of the skill or knowledge in the art. The embodiments described above are intended to illustrate the best mode for carrying out the technical idea of the present disclosure, and various modifications required for specific applications and uses of the present disclosure are also possible. Therefore, the detailed description of the present disclosure is not intended to limit the present disclosure to the disclosed embodiments. In addition, the appended claims should be interpreted as covering other embodiments as well.

The invention claimed is:
1. A tibial alignment device comprising:
   an upper part configured to be capable of being coupled to a tibial cutting guide during a total knee arthroplasty; and a lower part coupled to the upper part to be vertically slidable, wherein the upper part comprises a cutting guide coupling part configured to mount the tibial cutting guide on the upper part, and a connection part configured to connect the upper part and the lower part to each other, and the lower part comprises an ankle forceps part configured to be fixed to an ankle of a subject to be treated so as to fix the tibial alignment device, wherein the cutting guide coupling part may be coupled to or separated from the tibial cutting guide at various angles.

2. The tibial alignment device of claim 1, wherein the cutting guide coupling part comprises a fastening member configured to be capable of being coupled to the tibial cutting guide so as to be vertically movable, and a reception member configured to slidably receive the fastening member.

3. The tibial alignment device of claim 2, wherein the fastening member comprises a coupling part that protrudes in an insertion direction of the cutting guide coupling part at an upper end of the fastening member to be inserted into and coupled to the tibial cutting guide, the reception member comprises a coupling part that protrudes in the insertion direction of the cutting guide coupling part at an upper end of the reception member to be inserted into and coupled to the tibial cutting guide, and the coupling part of the fastening member is configured to be capable of adjusting a gap with respect to the coupling part of the reception member so that the tibial alignment device can be detached from and attached to the tibial cutting guide at various angles.

4. The tibial alignment device of claim 3, wherein the gap between the coupling part of the fastening member and the coupling part of the reception member is widened, and thus the coupling parts are placed in a locked state in which the coupling parts are firmly coupled with the tibial cutting guide, and the gap between the coupling part of the fastening member and the coupling part of the reception member is narrowed, and thus the coupling parts are placed in an unlocked state in which the coupling parts are loosely coupled to the tibia cutting guide.

5. The tibial alignment device of claim 4, wherein the cutting guide coupling part comprises a lever member configured to adjust the gap between the coupling part of the fastening member and the coupling part of the reception member.

6. The tibial alignment device of claim 5, wherein the lever member comprises a rotating body part configured to enable rotation of the lever member, a leaf spring part configured to press the fastening member upward in the locked state, a handle part configured to be capable of adjusting the locked state and the unlocked state of the lever member, a rotation prevention step configured to prevent rotation of the lever member in the locked state, and a groove part forming a space between the leaf spring part and the rotating body part.

7. The tibial alignment device of claim 6, wherein the cutting guide coupling part comprises close contact means configured to tighten the gap between the coupling part of the fastening member and the coupling part of the reception member in the unlocked state.

8. The tibial alignment device of claim 7, wherein the coupling part of the fastening member has a coupling surface comprising a protruding surface one end of which protrudes upward.

9. The tibial alignment device of claim 8, wherein the coupling surface comprises a concave surface formed in a curved surface and recessed to an inside of the coupling part, and a convex surface extending from the concave surface and protruding to an outside of the coupling part, the convex surface constituting the protruding surface.

10. The tibial alignment device of claim 9, wherein the fastening member comprises a stopper configured to limit an insertion depth of the coupling part.

11. The tibial alignment device of claim 1, wherein the upper part comprises a fine adjustment part configured to be capable of finely adjusting a height of the cutting guide.

12. The tibial alignment device of claim 1, wherein the ankle forceps part comprises a hook-shaped ankle forceps fixed to an ankle of a subject to be treated, an ankle forceps connection part configured to connect the ankle forceps and the connection part of the lower part to each other, a sliding adjustment part configured to slide the ankle forceps connection part in an anterior or posterior direction of the subject to be treated, a rachet button configured to fix a position of the ankle forceps connection part, and a connection bolt configured to prevent separation of the rachet button.

13. The tibial alignment device of claim 12, wherein the ankle forceps part has a washing groove configured to facilitate inflow of washing water so as to increase washing efficiency.

14. The tibial alignment device of claim 13, wherein the sliding adjustment part comprises a cleaning groove penetrating both side surfaces thereof into which the rachet button is inserted, and the rachet button comprises a cleaning groove penetrating both side surfaces of a lower end thereof into which the connection bolt is inserted.

15. A tibial alignment device comprising:

an upper part configured to be capable of being coupled to a tibial cutting guide during a total knee arthroplasty; and a lower part coupled to the upper part to be vertically slidable, wherein the upper part comprises a cutting guide coupling part configured to mount the tibial cutting guide on the upper part, and a connection part configured to connect the upper part and the lower part to each other, and the lower part comprises an ankle forceps part configured to be fixed to an ankle of a subject to be treated so as to fix the tibial alignment device, a height adjustment part configured to be capable of adjusting a coupling length between the upper and lower parts, and a connection part connecting the height adjustment part and the ankle forceps part, and wherein the height adjustment part comprises a first member configured to connect the connection part of the upper part and the connection part of the lower part to each other, a second member configured to adjust a vertical movement of the connection part of the upper part, and an elastic member configured to fix a position of the second member.

16. The tibial alignment device of claim 15, wherein, when the connection part is in contact with the second member, the second member is placed in the locked state in which lower rod is fixed, and when the connection part of the upper part and the second member forms a gap therebetween, the second member is placed in the unlocked state in which the connection part of the upper part is vertically slidable.

17. The tibial alignment device of claim 16, wherein the second member comprises a contact part configured to come into contact with the connection part of the upper part, a rotation coupling part configured to rotate the second member, and a handle part configured to be capable of adjusting the locked state and the unlocked state of the second member.

18. The tibial alignment device of claim 17, wherein the contact portion comprises a reception hole through which the connection part of the upper part passes, and the reception hole is formed to allow the connection part of the upper part and the second member to come into contact when the second member is in the locked state.

* * * * *